(12) United States Patent
Yoshimasa et al.

(10) Patent No.: US 7,625,363 B2
(45) Date of Patent: Dec. 1, 2009

(54) ABSORBENT ARTICLE

(75) Inventors: Wataru Yoshimasa, Kagawa (JP); Noritatsu Tamagawa, Kagawa (JP); Kazuya Nishitani, Kagawa (JP)

(73) Assignee: Uni-Charm Corporation, Ehime-Ken (JP)

( * ) Notice: Subject to any disclaimer, the term of this patent is extended or adjusted under 35 U.S.C. 154(b) by 354 days.

(21) Appl. No.: 10/841,325

(22) Filed: May 7, 2004

(65) Prior Publication Data

US 2004/0243084 A1    Dec. 2, 2004

(30) Foreign Application Priority Data

May 27, 2003    (JP) .............................. 2003-148629

(51) Int. Cl.
*A61F 13/15*    (2006.01)
(52) U.S. Cl. ........................... 604/385.101; 604/385.01
(58) Field of Classification Search .......... 604/385.101, 604/385.01
See application file for complete search history.

(56) References Cited

U.S. PATENT DOCUMENTS

| | | | |
|---|---|---|---|
| 4,676,786 A * | 6/1987 | Nishino | 604/378 |
| 5,399,175 A * | 3/1995 | Glaug et al. | 604/385.101 |
| 5,514,120 A * | 5/1996 | Johnston et al. | 604/378 |
| 5,961,505 A * | 10/1999 | Coe et al. | 604/378 |
| 6,096,016 A | 8/2000 | Tsuji et al. | |
| 6,241,714 B1 * | 6/2001 | Raidel et al. | 604/378 |
| 6,326,525 B1 * | 12/2001 | Hamajima et al. | 604/378 |
| 6,362,391 B1 * | 3/2002 | Mizutani et al. | 604/379 |
| 6,575,948 B1 * | 6/2003 | Kashiwagi et al. | 604/385.101 |
| 6,703,538 B2 * | 3/2004 | Lassen et al. | 604/378 |

FOREIGN PATENT DOCUMENTS

| | | | |
|---|---|---|---|
| JP | 02-257951 A1 | | 10/1990 |
| JP | 7-500759 A1 | | 5/1993 |
| JP | 8-511706 A1 | | 12/1996 |
| JP | 09-234221 A | | 9/1997 |
| JP | 2000024028 A | * | 1/2000 |
| JP | 2000-140015 A | | 5/2000 |
| JP | 2000-225146 A1 | | 8/2000 |
| JP | 2001-137284 A1 | | 5/2001 |

* cited by examiner

*Primary Examiner*—Tatyana Zalukaeva
*Assistant Examiner*—Lynne Anderson
(74) *Attorney, Agent, or Firm*—Darby & Darby P.C.

(57) ABSTRACT

Disclosed is an absorbent article having a center absorbent element on a backsheet. The center absorbent element has a center absorbent sheet covered with a center topsheet. The center absorbent sheet is formed with a plurality of projections, wherein longitudinal guide grooves are defined between transversely adjacent projections, transverse guide grooves are defined between longitudinally adjacent projections for communication between the longitudinal guide grooves. The longitudinal guide grooves are dimensioned to extend over at least two projections aligned in the longitudinal direction.

18 Claims, 14 Drawing Sheets

Fig. 14
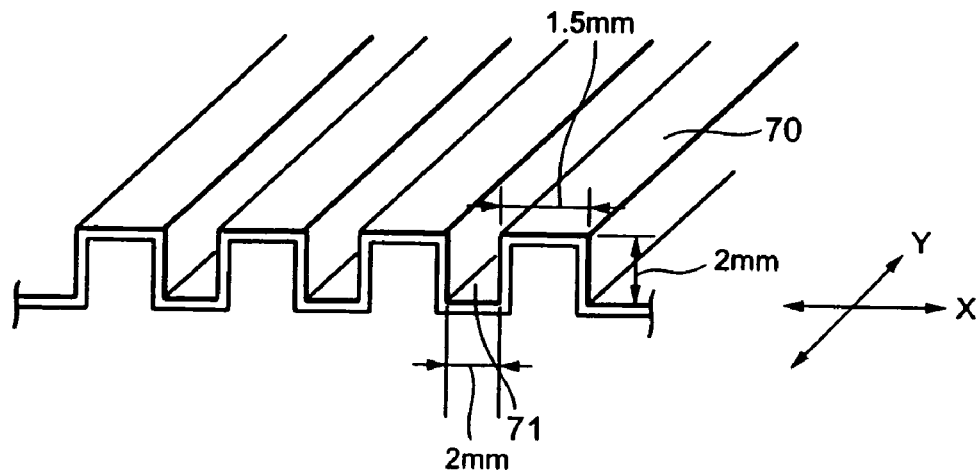
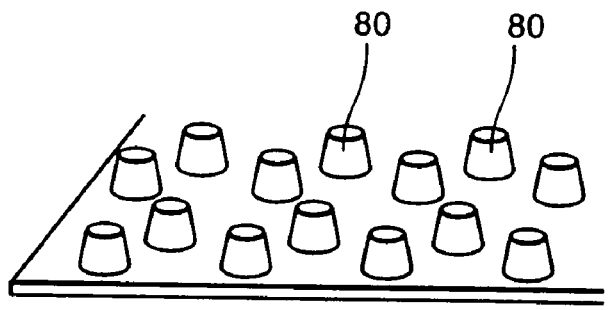
Fig. 15 A
Fig. 15 B
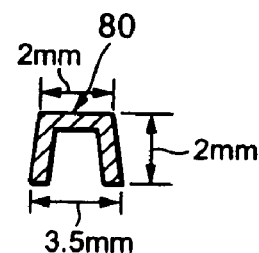
Fig. 15 C
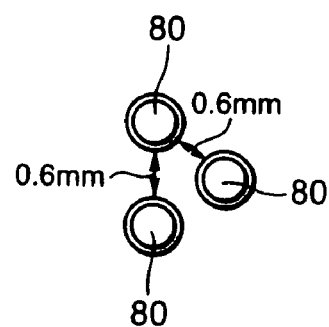

ABSORBENT ARTICLE

BACKGROUND OF THE INVENTION

1. Field of the Invention

The present invention relates to an absorbent article such as sanitary napkin, panty liner for absorption of woman's vaginal discharge, incontinence pad, auxiliary absorbent pad for diaper, and disposable diaper, more particularly, relates to an absorbent article in which liquid applied to its skin-side surface can be longitudinally diffused for rapid absorption.

2. Description of the Related Art

Absorbent articles, such as sanitary napkin for absorption of woman's menstrual blood, are typically constructed to include a liquid-impermeable backsheet, an absorbent layer disposed on the backsheet for absorption and retention of liquid, and a liquid-permeable topsheet covering a skin-side surface of the absorbent layer. Liquid discharged from the body may pass through the topsheet mainly in a central portion of the absorbent article for subsequent absorption and retention by the absorbent layer.

In absorbent articles of this kind, it is preferred that the liquid absorption rate is high and the liquid absorption capacity is large, as well as that transverse liquid leakage hardly occurs. Accordingly, the following Patent Publications disclose absorbent articles which are intended to let applied liquid diffuse mainly along a longitudinal direction for effective prevention of transverse liquid leakage.

Patent Publication 1:
Japanese Unexamined Patent Publication No. H8-511706

Patent Publication 2:
Japanese Unexamined Patent Publication No. H2-257951

Patent Publication 3:
Japanese Unexamined Patent Publication No.2000-225146

In the absorbent article disclosed in the Patent Publication 1, a liquid orientation component is disposed beneath a topsheet appearing on the skin-side surface. As shown in FIG. 11 of the Patent Publication 1, the liquid orientation component is formed with longitudinal ribs which project toward the skin-side and extend continuously longitudinally in a parallel arrangement. This absorbent article is aimed at guiding liquid, which has passed through the topsheet, in longitudinal movement with the liquid orientation component so as to prevent transverse leakage.

However, since the liquid orientation component is formed of an apertured plastic film and the longitudinal ribs are formed to extend continuously longitudinally, liquid applied to grooves each defined between adjacent longitudinal ribs will take long time to migrate to the absorbent layer, so that the liquid tends to remain in the grooves. Accordingly, this absorbent article presents a problem of delay in the liquid absorption rate.

In FIG. 10 of the Patent Publication 1, there is also disclosed another embodiment of the liquid orientation component being a hydrophobic film structure having a large number of projections, which are of a circular shape as viewed from above, regularly arranged thereon. In this liquid orientation component, however, it is not easy to guide liquid in longitudinal movement, or rather, the projections may possibly block liquid diffusion.

On the other hand, the Patent Publications 2 and 3 disclose a structure in which separate absorbent bodies each extending continuously longitudinally are so disposed that liquid applied to the individual absorbent bodies can be diffused along the longitudinal direction for prevention of transverse liquid diffusion.

In the absorbent articles disclosed in Patent Publications 2 and 3, however, since the separate absorbent bodies are similar in structure, liquid applied to a central absorbent body, for example, may be diffused uniformly in both longitudinal and transverse directions inside the absorbent body. This results in easy migration of liquid to adjacent absorbent bodies, so that when a large amount of liquid is applied, it will be difficult to certainly prevent transverse liquid leakage.

SUMMARY OF THE INVENTION

The present invention has been worked out in view of the shortcomings in the prior art set forth above. It is therefore an object of the present invention to provide an absorbent article which is effective in guiding liquid in longitudinal movement, as well as can absorb liquid rapidly, effectively preventing transverse leakage.

According to the present invention, there is provided an absorbent article comprising a liquid-permeable topsheet on a skin-side, a backsheet on a garment-side, and an absorbent sheet disposed therebetween for liquid absorption, the absorbent sheet being three-dimensionally shaped in a thickness direction to provide a plurality of projections, each of which is so raised toward the skin-side as to define a hollow opening toward the garment-side and dimensioned to be longer in a longitudinal direction of the article than in a transverse direction of the article when viewed from the skin-side, longitudinal guide grooves being defined between transversely adjacent projections, transverse guide grooves being defined between longitudinally adjacent projections for communication between the longitudinal guide grooves, the longitudinal guide grooves being dimensioned to extend over at least two projections aligned in the longitudinal direction.

In the absorbent article of the present invention, liquid applied thereto may be guided not only in longitudinal movement by the longitudinal guide grooves formed in the absorbent sheet, but also in transverse movement by the transverse guide grooves. However, since the longitudinal guide grooves are longer than the transverse guide grooves, the liquid can be diffused more easily along the longitudinal direction than along the transverse direction. In addition, since the absorbent sheet itself has the ability to absorb liquid, liquid flowing through the guide grooves can be absorbed by the absorbent sheet so rapidly as not to stay in the guide grooves.

On a transversely extending straight line passing one transverse guide groove, projections and transverse guide grooves may alternate with each other with the longitudinal guide grooves therebetween.

In this construction, since adjacent transverse guide grooves do not lie on the transversely extending straight line, there may be prevented excessive transverse diffusion of liquid as well as transverse leakage of liquid.

In the present invention, preferably, a B2/A2 ratio is larger than a B1/A1 ratio, where A1 represents a sectional area of the hollow of each projection and B1 represents a sectional area of a hollow of each transverse guide groove with the absorbent sheet being cut along a longitudinally extending section line which passes a top of one projection, while A2 represents a sectional area of the hollow of each projection and B2 represents a sectional area of a hollow of each longitudinal guide groove with the absorbent sheet being cut along a transversely extending section line which crosses transversely adjacent projections.

With this construction, liquid can be easily guided within the longitudinal guide grooves and diffused along the longitudinal direction.

In the present invention, also preferably, a B1/A1 ratio is smaller at opposite side portions of the absorbent sheet than at a position coinciding with a longitudinally extending centerline of the article, where A1 represents a sectional area of the hollow of each projection and B1 represents a sectional area of a hollow of each transverse guide groove with the absorbent sheet being cut along a longitudinally extending section line which passes a top of one projection.

In an alternative, a B2/A2 ratio maybe smaller at opposite side portions of the absorbent sheet than at a position coinciding with a longitudinally extending centerline of the article, where A2 represents a sectional area of the hollow of each projection and B2 represents a sectional area of a hollow of each longitudinal guide groove with the absorbent sheet being cut along a transversely extending section line which crosses transversely adjacent projections.

In another alternative, the projections may have such different longitudinal dimensions as to be longer at opposite side portions of the absorbent sheet than at a position coinciding with a longitudinally extending centerline of the article.

With any one of these constructions, liquid at a central portion of the absorbent sheet can be easily diffused longitudinally, and liquid trying to flow transversely can be blocked at the side portions of the absorbent sheet, resulting in effective prevention of transverse leakage from the absorbent sheet.

In the present invention, only the absorbent sheet may be provided as a layer having the ability to absorb liquid, but it is also possible that a liquid absorption/retention layer is disposed on a garment-side surface of the absorbent sheet and kept in contact with individual bottoms of the longitudinal and the transverse guide grooves of the absorbent sheet.

With the liquid absorption/retention layer being provided beneath the absorbent sheet, liquid absorbed by the absorbent sheet may migrate to the liquid absorption/retention layer, increasing the liquid absorption capacity of the absorbent article.

In the absorbent sheet, preferably, walls of the projections extending alongside the longitudinal guide grooves have a lower density than tops of the projections and the bottoms of the longitudinal and the transverse guide grooves.

With this construction, liquid flowing through the longitudinal guide grooves can pass through the low-density walls into the hollows of the projections, facilitating migration into the underlying liquid absorption/retention layer.

The present invention may also be constructed such that longitudinally extending side absorbent elements are provided at transversely opposite sides of a longitudinally extending center absorbent element, and garment-side surfaces of the individual absorbent elements are supported by the backsheet, wherein the center absorbent element includes the absorbent sheet and the topsheet covering a skin-side surface, as well as both side edges, of the absorbent sheet; each side absorbent element includes a side absorbent sheet for liquid absorption and a side topsheet covering a skin-side surface, as well as both side edges, of the side absorbent sheet, wherein the liquid absorption/retention layer extends from beneath a garment-side surface of the center absorbent element to beneath garment-side surf aces of the side absorbent elements.

With the absorbent sheet being thus provided in the center absorbent element, liquid applied to the center absorbent element can be so guided in longitudinal move as not to diffuse transversely, whereby liquid hardly migrates to the side absorbent elements, effectively preventing transverse leakage.

Here, the absorbent article may be allowed to bend more easily at boundaries between the center absorbent element and the side absorbent elements than at the center absorbent element and at the side absorbent elements, wherein when the absorbent article is attached to an undergarment and subjected to a transverse pressure, the center absorbent element may be so deformed toward the wearer's body as to come into close contact with an excretory part of the wearer's body.

When an equal amount of liquid is applied to a skin-side surface of the center absorbent element and a skin-side surface of the side absorbent element, it is preferred that the center absorbent element has a higher liquid absorption rate than the side absorbent element.

In this case, for example, the topsheet of the center absorbent element may be more permeable to liquid than the side topsheet.

BRIEF DESCRIPTION OF THE DRAWINGS

The present invention will be understood more fully from the detailed description given hereinafter and from the accompanying drawings of the preferred embodiments of the present invention, which, however, should not be taken to be limitative to the invention, but are for explanation and understanding only.

In the drawings:

FIG. 14 is a perspective view showing a portion of an absorbent sheet used for Comparative Example 2 in experiment; and FIG. 15A is a perspective view showing a portion of an absorbent sheet used for Comparative Example 3 in experiment; FIG. 15B is an enlarged sectional view of each projection shown in FIG. 15A, and FIG. 15C is a top plan view showing some of the projections shown in FIG. 15A.

DESCRIPTION OF THE PREFERRED EMBODIMENT

The present invention will be discussed hereinafter in detail in terms of the preferred embodiments according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscurity of the present invention.

In the present invention, the absorbent article may be embodied in a sanitary napkin whose primary object is to absorb menstrual blood discharged from the vaginal opening of a woman or the like. It should be noted that the absorbent article, as well as its individual components, has two major surfaces: of which one surface intended to be worn toward the wearer's crotch is referred to as "skin-side surface", while the other surface is referred to as "garment-side surface" regardless of whether a garment is worn outside the absorbent article or not. In the following description, "Y-direction" refers to a longitudinal direction of the absorbent article; "X-direction" refers to a transverse direction perpendicular to the longitudinal direction.

Figure 1:
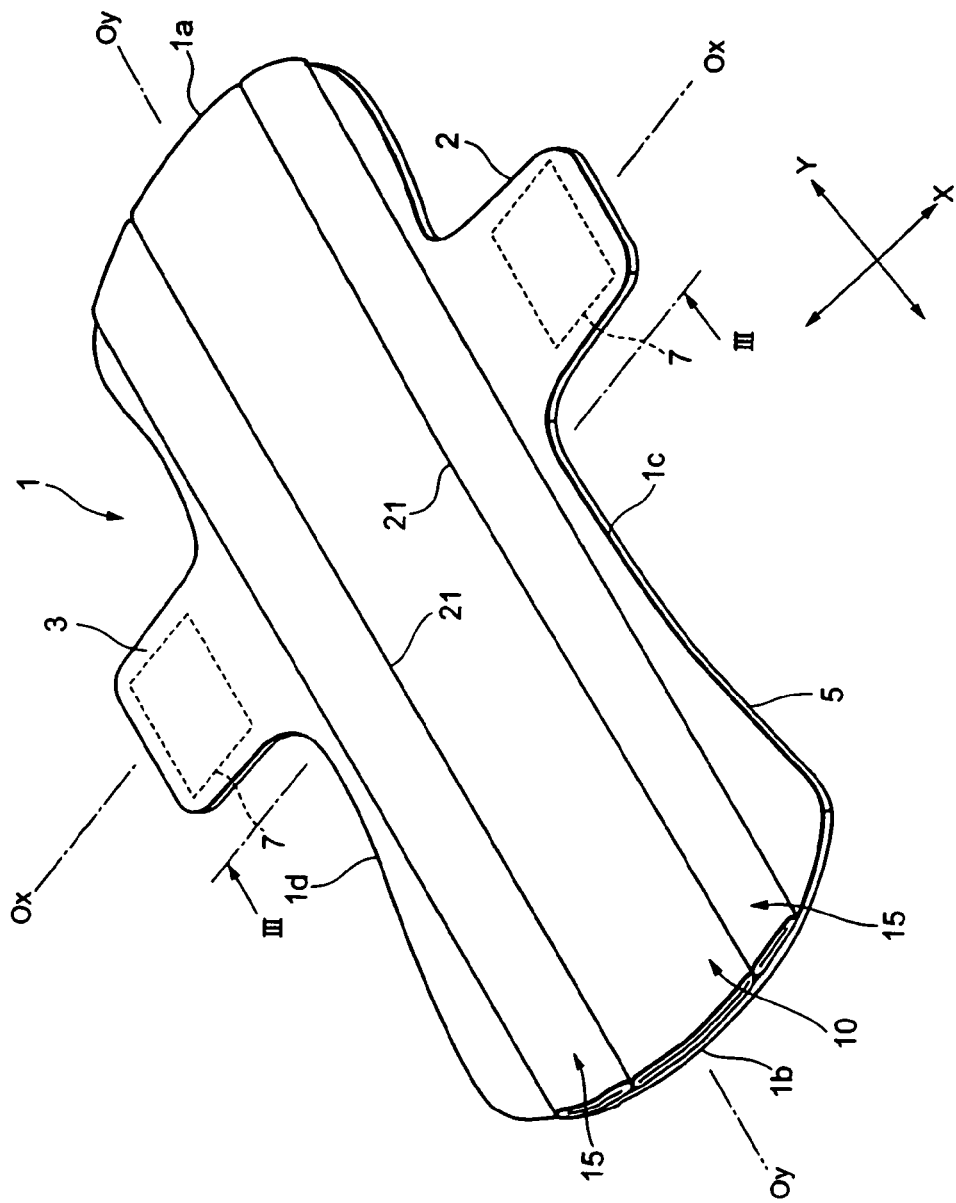
FIG. 1 is a perspective view showing a sanitary napkin being a first embodiment of the absorbent article according to the present invention.
Figure 2:
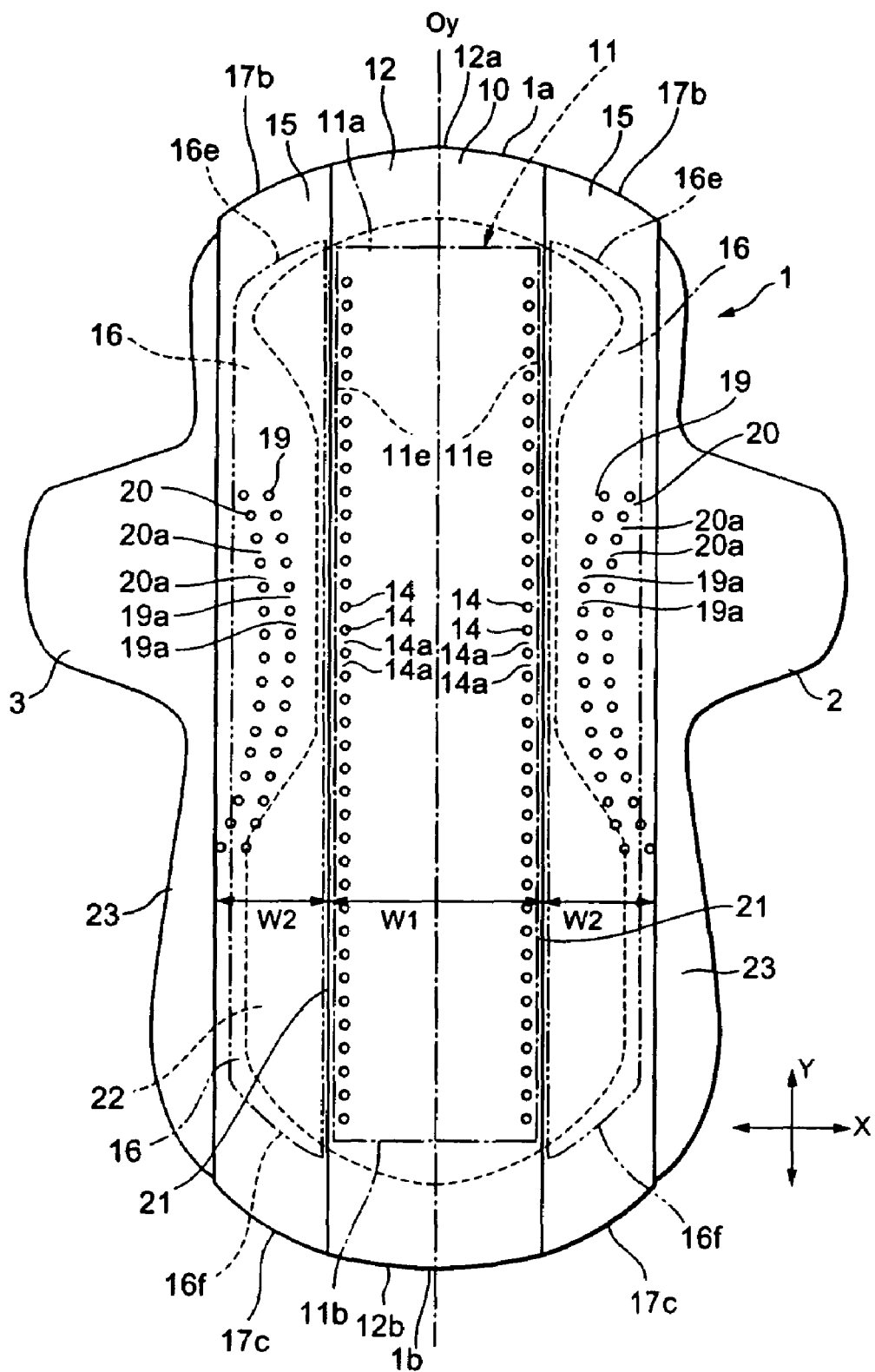
FIG. 2 is a top plan view of the sanitary napkin of FIG. 1.
Figure 3:
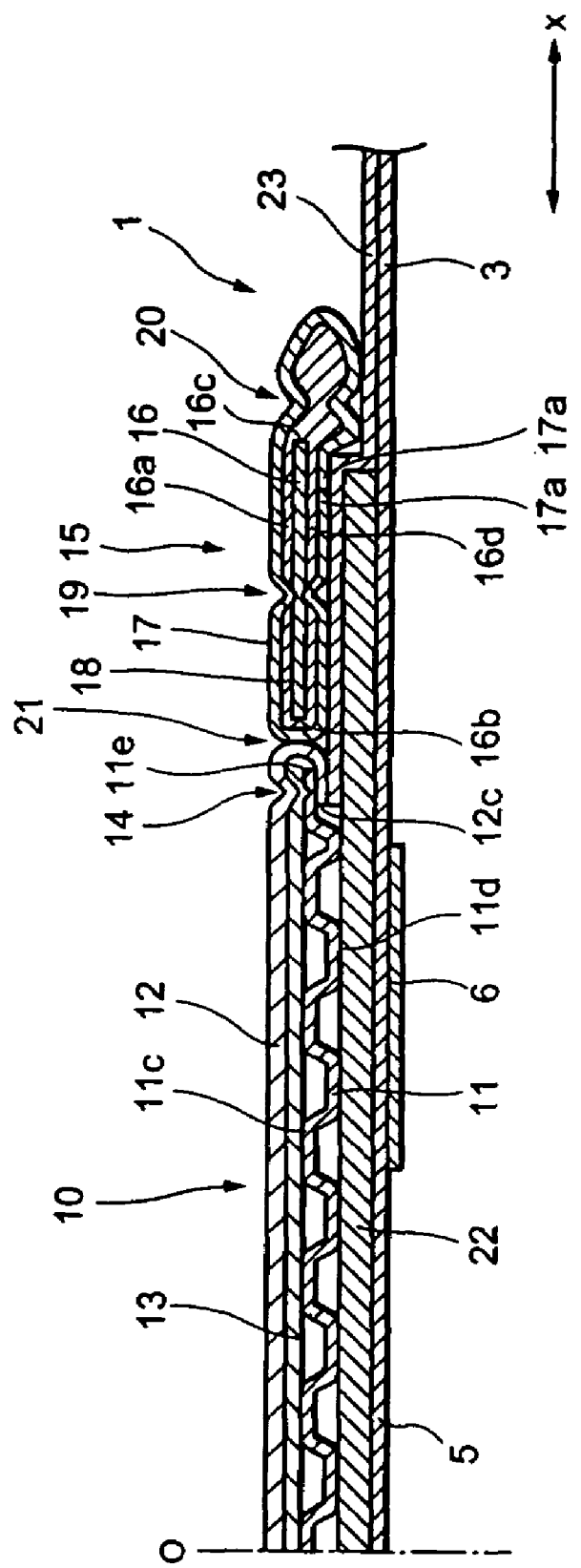
FIG. 3 is an enlarged sectional view of a portion of the sanitary napkin of FIG. 1, wherein only a right half of a sectional view taken along the line III-III with respect to the longitudinally extending centerline is shown on an enlarged scale.

FIG. 1 is a perspective view showing a sanitary napkin 1 being a first embodiment of the absorbent article according to the present invention, with its skin-side surface directed upward; FIG. 2 is a top plan view of the sanitary napkin of FIG. 1; and FIG. 3 is an enlarged sectional view of a portion of the sanitary napkin of FIG. 1, wherein only a right half of a sectional view taken along the line III-III with respect to the longitudinally extending centerline Oy-Oy is shown on an enlarged scale. Here, FIG. 2 shows compressed/recessed dot-like portions that are formed in the skin-side surface by embossing, but these compressed/recessed portions are omitted from FIG. 1.

When viewed from above, the sanitary napkin 1 is of such an elongated configuration as to be longer in the Y-direction than in the X-direction. The sanitary napkin 1 has an arcuate front end edge 1a and an arcuate rear end edge 1b, which are curved forward and rearward, respectively. On the other hand, right and left side edges 1c, 1d, which extend longitudinally, are curved toward the longitudinally extending center line Oy-Oy. The distance between the right and the left side edges 1c, 1d, i.e., the width of the sanitary napkin 1 is larger on the side of the rear end edge 1b, which is intended to be mainly applied to the wearer's buttocks, than on the side of the front end edge 1a, which is intended to be mainly applied to the crotch.

In the sanitary napkin 1, a line extending transversely and passing through a particular position, which almost coincides with a longitudinal center of the vaginal opening when the sanitary napkin 1 is applied to the woman's crotch, is called transverse reference line Ox-Ox. Along the transverse reference line Ox-Ox, the sanitary napkin 1 is provided with wings 2, 3 to have the right and the left side edges 1c, 1d bulged locally in the transverse direction (X-direction). The sanitary napkin 1 is symmetrical about the longitudinally extending centerline Oy-Oy.

As shown in the sectional view of FIG. 3, the sanitary napkin 1 has a backsheet 5 on its garment-side surface. The backsheet 5 is impermeable to liquid but breathable and may be a porous polyethylene (PE) or polypropylene (PP) film having a thickness of about 15-50 μm. When viewed from above, the backsheet 5 has the same shape as the sanitary napkin 1, and therefore, the backsheet 5 has peripheral edges coinciding with the front end edge 1a, the rear end edge 1b, the right side edge 1c, and the left side edge 1d, respectively.

On a garment-side surface of the backsheet 5, there are disposed pressure-sensitive adhesive layers 6, 6. These adhesive layers 6, 6 are individually applied in the shape of a longitudinally extending strip, centrally of the napkin. Pressure-sensitive adhesive layers 7, 7 are also applied on the garment-side surface in the wings 2, 3. In the sanitary napkin 1 before use, the pressure-sensitive adhesive layers 6, 6 and the pressure-sensitive adhesive layers 7, 7 are covered and protected by a release sheet.

Above a skin-side surface of the backsheet 5, there are disposed a center absorbent element 10, which extends in the longitudinal direction, and side absorbent elements 15, 15, which are on right and left sides of the center absorbent element 10 and individually extend also in the longitudinal direction. The center absorbent element 10, as well as the side absorbent elements 15, 15, extends over the whole sanitary napkin 1 in the longitudinal direction.

As shown in FIG. 3, the center absorbent element 10 includes an elongated center absorbent sheet 11 and a center topsheet 12 covering a skin-side surface 11c of the center absorbent sheet 11, as well as longitudinally extending side edges 11e, 11e. As shown in FIG. 2, the center absorbent sheet 11 is of an elongated rectangular shape with its front and rear end edges 11a, 11b being positioned inside the front and the rear end edges 1a, 1b of the sanitary napkin 1. On the other hand, the center topsheet 12 has front and rear end edges 12a, 12b which almost coincide with the front and the rear end edges 1a, 1b of the sanitary napkin 1.

Side portions 12c, 12c of the center topsheet 12 are folded back against a garment-side surface 11d of the center absorbent sheet 11 to cover the side edges 11e, 11e of the center absorbent sheet 11, as shown in FIG. 3. On the garment-side of the center absorbent element 10, therefore, most of the garment-side surface 11d of the center absorbent sheet 11 remains uncovered by the center topsheet 12.

Between the skin-side surface 11c of the center absorbent sheet 11 and the center topsheet 12, there is disposed a second topsheet 13, as shown in FIG. 3. The second topsheet 13 is substantially coextensive with the center topsheet 12 so as to cover the whole skin-side surface 11c of the center absorbent sheet 11.

The center absorbent element 10 has a plurality of compressed/recessed portions 14 that are arranged at a constant pitch in the longitudinal direction in symmetrical relation with respect to the longitudinally extending centerline Oy-Oy, as shown in FIG. 2. The compressed/recessed portions 14 are aligned linearly along the longitudinal direction, and in the individual compressed/recessed portions 14, the center topsheet 12, the second topsheet 13, and the center absorbent sheet 11 are locally heated under pressure so as to be bonded together.

In the individual compressed/recessed dot-like portions 14, the center topsheet 12, the second topsheet 13, and the center absorbent sheet 11 are fusion-bonded together so as to be almost filmy; in intermediate portions 14a between longitudinally adjacent compressed/recessed portions 14, the center topsheet 12, the second topsheet 13, and the center absorbent sheet 11 are also compressed. As a result, the skin-side surface of the sanitary napkin 1 is recessed not only at the compressed/recessed portions 14 but also at the intermediate portions 14a, thereby forming compressed grooves along the arranging direction of the compressed/recessed portions 14. Here, the compressed/recessed dot-like portions 14 thus aligned may be replaced by compressed grooves formed by fusion-bonding the sheets such that the resulting filmy region extends linearly in the longitudinal direction.

The side absorbent elements 15, 15 are similar in shape and structure to each other.

The each individual side absorbent element 15 includes an elongated side absorbent sheet 16, a third topsheet 18 to be wrapped around the side absorbent sheet 16, and a side topsheet 17 to be wrapped around the side absorbent sheet 16 and the third topsheet 18. That is, the side absorbent sheet 16 is covered with the third topsheet 18 and the side topsheet 17 not only at its whole skin-side surface 16a but also at its inner side edge 16b facing the center absorbent element 10, outer side edge 16c, and garment-side surface 16d. Here, the side topsheet 17 has two terminal ends 17a, 17a which are in contact with each other on the garment-side, as shown in FIG. 3, or opposed to each other with a given clearance therebetween.

As shown in FIG. 2, a front end edge 16e of the side absorbent sheet 16 is positioned slightly inside the front end edge 1a of the sanitary napkin 1, and a rear end edge 16f of the side absorbent sheet 16 is positioned slightly inside the rear end edge 1b of the sanitary napkin 1. On the other hand, the side topsheet 17 has front and rear end edges 17b, 17c, which are quite similar in shape to the front and the rear end edges 1a, 1b, respectively. When viewed from above as in the top plan view of FIG. 2, the third topsheet 18 is coextensive with the topsheet 17.

The each individual side absorbent element 15 is formed with inner compressed/recessed portions 19 and outer compressed/recessed portions 20, which are arranged in the longitudinal direction (Y-direction) as shown in FIG. 2. More specifically, both the inner and the outer compressed/recessed portions 19, 20 are dot-like portions arranged along an arcuate line that is curved toward the longitudinal centerline Oy-Oy. In the individual inner compressed/recessed portions 19, the side topsheet 17, the third topsheet 18, and the side absorbent sheet 16 are locally heated under pressure; in the individual outer compressed/recessed portions 20, the side topsheet 17 and the third topsheet 18 are locally heated under pressure.

In the inner compressed/recessed portions 19, the side topsheet 17, the third topsheet 18, and the side absorbent sheet 16 are compressed so as to be almost filmy. Also in intermediate portions 19a between adjacent inner compressed/recessed portions 19, the side topsheet 17, the third topsheet 18, and the side absorbent sheet 16 are compressed. As a result, the skin-side surface of the sanitary napkin 1 is recessed not only at the inner compressed/recessed portions 19 but also at the intermediate portions 19a, thereby forming arcuate compressed grooves along the arranging direction of the inner compressed/recessed portions 19.

Also in the outer compressed/recessed portions 20 and intermediate portions 20a between adjacent outer compressed/recessed portions 20, the sheets are compressed and recessed as in the inner compressed/recessed portions 19 and the intermediate portions 19a.

Here, the inner and the outer compressed/recessed dot-like portions 19, 20 thus arranged may be replaced by inner and outer compressed grooves formed by fusion-bonding the sheets such that the resulting filmy region extends in the shape of an arcuate line.

As shown in FIGS. 2 and 3, a liquid absorption/retention layer 22 is disposed on the backsheet 5. The liquid absorption/retention layer 22 has a larger liquid retention capacity per unit area than the center absorbent sheet 11 and the side absorbent sheet 16. As shown in FIG. 2, the liquid absorption/retention layer 22 is of such an hourglass shape that its center portion is disposed between the center absorbent element 10 and the backsheet 5 but its side portions are extended to between the side absorbent elements 15 and the backsheet 5. Here, the liquid absorption/retention layer 22 and the backsheet 5 are bonded together through a hot-melt type adhesive.

Most of the garment-side surface 11d of the center absorbent sheet 11, which remains uncovered by the center topsheet 12 on the garment-side of the center absorbent element 10, is bonded to the skin-side surface of the liquid absorption/retention layer 22 through a hot-melt type adhesive. This hot-melt type adhesive is applied so randomly as not to interfere with migration of liquid from the center absorbent sheet 11 to the liquid absorption/retention layer 22.

Between the side absorbent element 15 and the liquid absorption/retention layer 22, there is interposed a liquid-permeable soft sheet 23. The soft sheet 23 is bonded to the skin-side surface of the liquid absorption/retention layer 22 through a hot-melt type adhesive without interfering with liquid permeation, as well as bonded to the backsheet 5 outside the side absorbent element 15. The side absorbent element 15 is bonded to the skin-side surface of the soft sheet 23 through a hot-melt type adhesive that is applied so randomly as not to interfere with liquid permeation.

As shown in FIGS. 1 to 3, the central absorbent element 10 and the side absorbent elements 15, 15 are separate and distinct from each other, defining therebetween boundaries 21, 21.

Along the individual boundaries 21, 21, a portion of the center topsheet 12 covering the side edge 11e of the center absorbent sheet 11 and a portion of the side topsheet 17 covering the inner side edge 16b of the side absorbent sheet 16 are in contact with each other, as shown in FIG. 3, or opposed to each other with a given clearance therebetween. Therefore, the boundaries 21, 21 are grooves formed in the skin-side surface of the sanitary napkin 1 to reach the skin-side surface of the soft sheet 23. These grooves extend over the entire length of the sanitary napkin 1 in the longitudinal direction.

The sanitary napkin 1 is allowed to bend more easily at the boundaries 21, 21 than at the region covered with the center absorbent element 10 and at the regions covered with the side absorbent elements 15. In other words, the sanitary napkin 1 is formed with flexible lines extending longitudinally along the boundaries 21, 21.

When an equal amount of liquid is applied at an equal rate to the skin-side surface of the center absorbent element 10 and the skin-side surface of the side absorbent element 15, the time required for the center absorbent element 10 to absorb the liquid is shorter than the time required for the side absorbent element 15 to absorb the liquid. That is, when a similar liquid is applied to the skin-side surface, the center absorbent element 10 has a higher liquid absorption rate than the side absorbent element 15.

To this end, the center topsheet 12 is constructed to have a higher liquid permeation rate than the side topsheet 17.

For example, both the center topsheet 12 and the side topsheet 17 may be of a resin film or nonwoven fabric formed with a large number of liquid passage holes. In this case, the center topsheet 12 may have a higher opening area ratio (i.e., ratio of total opening area to whole sheet area) than the side topsheet 17. Alternatively, or additionally, the individual liquid passage holes in the center topsheet 12 may have a larger opening area than those in the side topsheet 17.

In addition to, or instead of, the above construction, the center topsheet 12 may have a higher hydrophilicity than the side topsheet 17.

For such a sheet formed with liquid passage holes, preferably, a resin film such as polyethylene (PE) having a basis weight of 20 to 50 g/m² may be apertured to have a large number of liquid passage holes. Alternatively, a laminate may be apertured to have a large number of liquid passage holes, wherein the laminate may be formed by laminating a resin film such as PE to a nonwoven fabric having a basis weight of 15 to 50 g/m², which is manufactured by thermally bonding a fiber web comprising sheath/core bicomponent synthetic fibers, of which the core is polypropylene (PP) and the sheath is polyethylene (PE) or the core is polyester (PET) and the sheath is PE.

The individual liquid passage holes may have an opening diameter within the range of 0.3 to 4.0 mm and the opening area ratio may fall within the range of 3 to 40% so as to appropriately set liquid permeation rates of the center topsheet 12 and the side topsheet 17.

Such resin films or laminates to be used for the center topsheet 12 and the side topsheet 17 may be similar in both opening area of individual liquid passage holes and opening area ratio. In this case, the center topsheet 12 may be made more hydrophilic than the side topsheet 17, as set forth above, with a hydrophilicity imparting agent such as surfactant applied to or kneaded in the center topsheet 12. Alternatively, or additionally, the side topsheet 17 may be made more water-repellent than the center topsheet 12 with a water-repellent material applied to or kneaded in the side topsheet 17.

In the case where both the center topsheet 12 and the side topsheet 17 are nonwoven fabrics, hydrophilicity of fibers constituting the center topsheet 12 may be made higher than hydrophilicity of fibers constituting the side topsheet 17.

For example, the center topsheet 12 may be a spunlaced or through-air bonded nonwoven fabric comprising a mixture of synthetic fibers such as PE, PP or PET (fineness of 1.1 to 4.4 dtex) and hydrophilic fibers such as rayon, pulp or cotton. Its basis weight may be 15 to 80 g/m². On the other hand, the side topsheet 17 may be a high-density nonwoven fabric with high barrier properties against liquid, such as meltblown nonwoven fabric comprising thin synthetic fibers (fineness of 0.3 to 1.1 dtex) and having a basis weight of about 20 to 80 g/m².

The nonwoven fabric may further be formed with liquid passage holes. In this case, the center topsheet 12 may be a nonwoven fabric formed with liquid passage holes, while the side topsheet 17 be a nonwoven fabric not formed with liquid passage holes.

Alternatively, the center topsheet 12 may be a highly liquid-permeable nonwoven fabric containing hydrophilic fibers, while the side topsheet 17 be a resin film which is formed with liquid passage holes but is of a relatively low liquid permeation rate.

Figure 4:
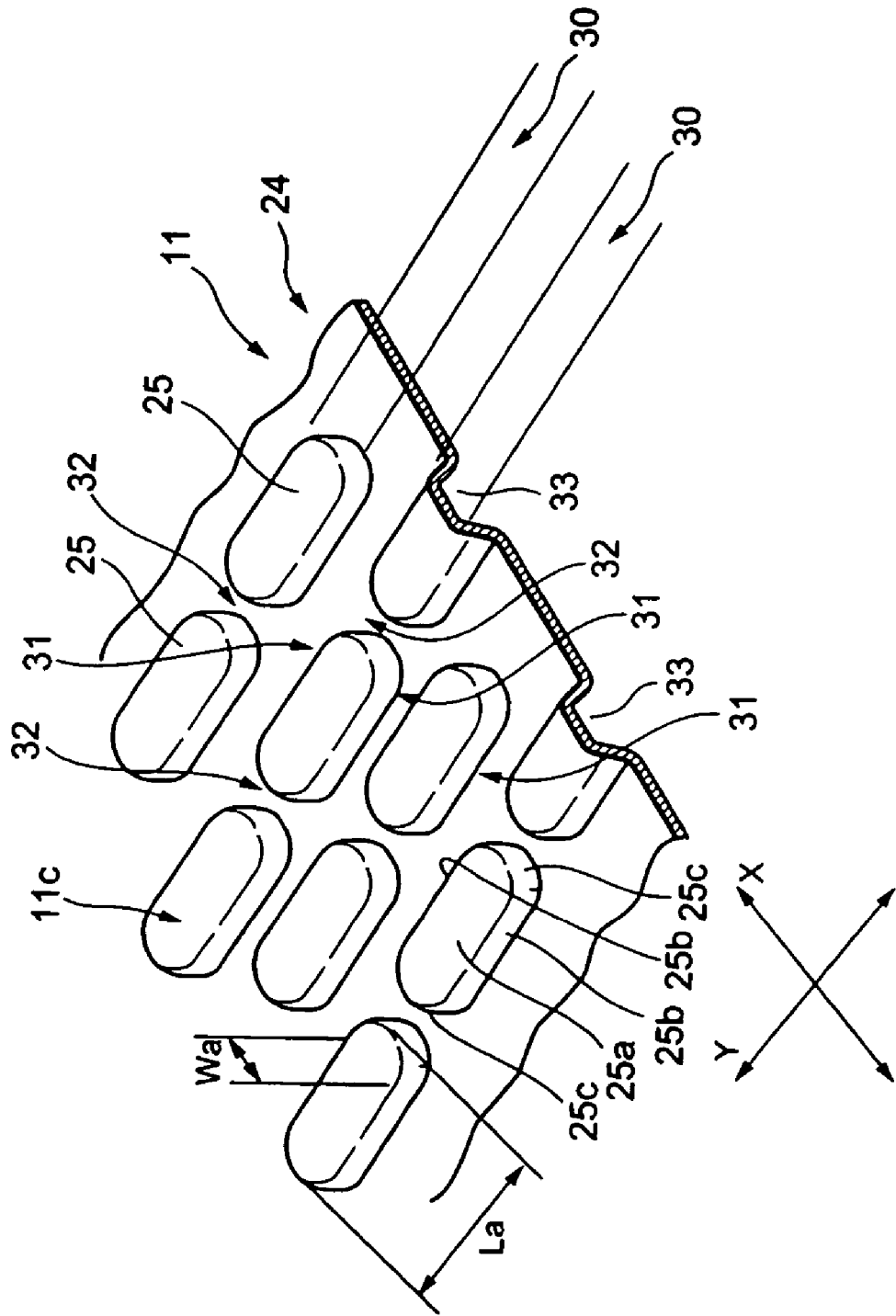
FIG. 4 is a perspective view of a portion of a center absorbent sheet according to the first embodiment.

FIG. 4 is a perspective view showing the center absorbent sheet 11 with its skin-side surface 11c directed upward, and FIG. 5A is a top plan view showing the center absorbent sheet 11 from the side of the skin-side surface 11c. FIG. 5B is a sectional view taken along the transversely extending section line B-B which crosses transversely adjacent projections, and FIG. 5C is a sectional view taken along the longitudinally extending section line C-C which transversely bisects longitudinally aligned projections.

The center absorbent sheet 11 comprises an absorbent sheet material 24 having the ability to absorb and retain liquid as well as the ability to retain shape, which is shaped in the sheet thickness direction to have such a three-dimensional configuration as shown in FIG. 4.

In order to provide the ability to retain shape, the absorbent sheet material 24 is preferably an air-laid nonwoven fabric (air-laid pulp), wherein fibers, after formation of fiber web through an air-laid process, are bonded to each other through a binder.

More specifically, the air-laid nonwoven fabric may be manufactured such that after pulp fibers are laid to have a basis weight within the range of 50 to 300 g/m², a heat fusible binder such as acrylic resin is dispersed therein in an amount of 5 to 20% by weight of the whole nonwoven fabric and then heated for bonding the pulp fibers to each other through the binder. Thus, the absorbent sheet material 24 having the ability to retain shape may be formed only of hydrophilic fibers (natural fibers).

Here, the air-laid nonwoven fabric may contain synthetic fibers, such as polyester (PET) having a fineness of 1.6 to 4.4 dtex and a fiber length of 1 to 10 mm, in an amount of 5 to 50% by weight, providing high wet strength to maintain bulkiness and three-dimensional configuration even after liquid absorption.

The air-laid nonwoven fabric may further contain superabsorbent polymer (SAP), but since too much superabsorbent polymer may possibly cause blocking, the superabsorbent polymer is preferably added in an amount of equal to or less than 10% by weight of the whole nonwoven fabric.

Alternatively, the absorbent sheet material 24 may be manufactured such that after pulp fibers are laid to have a basis weight within the range of 50 to 300 g/m², the pulp fibers, which are wrapped in tissue having a basis weight of 15 to 40 g/m², are compressed to have a density within the range of 0.05 to 0.15 g/cm³. It may also contain synthetic fibers, such as polyester (PET) having a fineness of 1.6 to 4.4 dtex and a fiber length of 1 to 10 mm, in an amount of 5 to 30% by weight, to thereby increase wet strength.

In order to increase wet strength, it is also possible to apply an adhesive such as hot-melt in an amount of about 3 to 10 g/m² into a spiral or comb pattern between the tissue and the pulp fibers.

For the center absorbent sheet 11, the absorbent sheet material 24 may be used alone or stacked on another absorbent sheet material 24 or another kind of absorbent sheet material. Alternatively, the single absorbent sheet material 24 may be folded in two or three.

The center absorbent sheet 11, which is shaped into the three-dimensional configuration shown in FIG. 4, preferably has a dry tensile breaking strength of equal to or greater than 2.5 N per 25 mm width in both the X- and the Y-directions. The tensile breaking strength is the maximum load measured when chucks are moved away from each other at a rate of 100 mm/min, wherein 25 mm width strips are cut out of the center absorbent sheet 11 along the X- and the Y-directions, respectively, and each specimen is held with the chucks at an initial chuck distance of 100 mm. It should be noted that the center absorbent sheet 11 has a wet tensile breaking strength preferably equal to or greater than 20%, more preferably equal to or greater than 30% the above-mentioned dry strength.

As shown in FIG. 4, the center absorbent sheet 11 is formed with a number of projections 25. The each individual projection 25 is so raised toward the skin-side as to define a hollow 33 opening toward the garment-side. The each individual projection 25 is elongated such that its longitudinal dimension La is larger than its transverse dimension Wa, measured at an arbitrary height position of the projection 25, and the each individual projection 25 is oval in shape when viewed from the skin-side.

The projections 25 are longitudinally arranged in rows 30 so that longitudinal guide grooves 31 are defined between adjacent rows 30. Longitudinally extending left side walls 25b of projections 25 arranged in one row 30 provide a right side wall of one longitudinal guide groove 31; conversely, longitudinally extending right side walls 25b of projections 25 arranged in one row 30 provide a left side wall of one longitudinal guide groove 31. In each row 30, moreover, since the projections 25 are arranged at spaced intervals, transverse guide grooves 32 are defined between longitudinally adjacent projections 25. In other words, each transverse guide groove 32 is defined between opposing ends 25c of longitudinally adjacent projections 25.

In the shown embodiment, the individual longitudinal guide grooves 31 extend continuously over the entire length of the center absorbent sheet 11 in the longitudinal direction. However, the individual longitudinal guide grooves 31 may be of separate short grooves arranged in the longitudinal direction, if they extend over at least two, preferably at least three, of the projections 25 longitudinally arranged in the rows 30.

On a transversely extending straight line D-D passing one transverse guide groove 32, projections 25 and transverse guide grooves 32 alternate with each other with the longitudinal guide grooves 31 therebetween, as shown in FIG. 5A. Between adjacent rows 30, therefore, none of the transverse guide grooves 32 are aligned with another in the transverse direction.

The area where tops 25a of the projections 25 are in close contact with the second topsheet 13 is preferably within the range of 25% to 65%, more preferably within the range of 40% to 55% of the area of the skin-side surface 11c of the center absorbent sheet 11. If the close contact area ratio is in excess of the above-mentioned range, the area ratio of the longitudinal guide grooves 31 to the center absorbent sheet 11 may be too small to effectively concentrate body fluid in the longitudinal guide grooves 31 for longitudinal migration. If the close contact area ratio is below the above-mentioned range, the area where the center absorbent sheet 11 is in contact with the second topsheet 13 may be too small, so that the ability to draw liquid applied to the center topsheet 12 into the center absorbent sheet 11 will be deteriorated to let the liquid stay in the center topsheet 12.

In FIGS. 5B and 5C, H1 represents a plane flush with the skin-side surface 11c of the center absorbent sheet 11, i.e., a plane in contact with the tops 25a of the projections 25 on the skin-side, while H2 represents a plane flush with the garment-side surface 11d of the center absorbent sheet 11, i.e., a plane in contact with bottoms 31a of the longitudinal guide grooves 31 and bottoms 32a of the transverse guide grooves 32 on the garment-side.

In the sectional view of FIG. 5C taken along the longitudinally extending section line C-C, A1 represents a sectional area of the hollow 33, which defined by an inner surface of the projection 25 and the plane H2, and B1 represents a sectional area of a space defined by outer surfaces of the projections 25 and the plane H1, i.e., a sectional area of a hollow of the transverse guide groove 32. In the sectional view of FIG. 5B taken along the transversely extending section line B-B, on the other hand, A2 represents a sectional area of the hollow 33, which defined by the inner surface of the projection 25 and the plane H2, and B2 represents a sectional area of the space defined by the outer surfaces of the projections 25 and the plane H1, i.e., a sectional area of the hollow of the transverse guide groove 32. These sectional areas are the averaged values from measurements at different positions.

B1 and B2 preferably fall within the range of 1 to 10 mm$^2$, more preferably fall within the range of 1.5 to 7 mm$^2$. If they are in excess of the above-mentioned range, the close contact area between the second topsheet 13 and the center absorbent sheet 1 may be too small to draw liquid into the center absorbent sheet 11 from the second topsheet 13. If they are below the above-mentioned range, on the other hand, thick body fluid such as menstrual blood may be difficult to diffuse along the longitudinal guide grooves 31 and the transverse guide grooves 32. Preferably, B1 may be smaller than B2. With B2 being larger B1, liquid may diffuse easily along the longitudinal direction to effectively prevent transverse liquid leakage.

On the other hand, A2 preferably falls within the range of 2 to 25 mm$^2$, more preferably falls within the range of 4 to 20 mm$^2$. With A2 being set within the above-mentioned range, the close contact area between the second topsheet 13 and the center absorbent sheet 11 may easily be set within the optimum range, as well as the hollow of the longitudinal guide groove 31 may be made suitable for guiding liquid.

The sectional area ratio of the hollow of the guide groove to the hollow of the projection 25 is expressed by B1/A1 when taken along the longitudinally extending section line C-C and expressed by B2/A2 when taken along the transversely extending section line B-B. Here, the ratio B2/A2 may be larger than the ratio B1/A1. (B1/A1):(B2/A2) is preferably from 1:1.2 to 1:10, more preferably from 1:1.5 to 1:5.

With the (B1/A1):(B2/A2) ratio being set within the above-mentioned range, liquid may easily enter the longitudinal guide grooves 31 to diffuse along the longitudinal direction through the longitudinal guide grooves 31. Moreover, even if a large amount of liquid is applied to one longitudinal guide groove 31, the transverse guide grooves 32 may allow migration of the liquid, which would otherwise stay in the longitudinal guide groove 31, to a next longitudinal guide groove 31, so that the ability to absorb liquid can be exploited over a large area of the center absorbent sheet 11. Here, since the transverse guide grooves 32 are formed so as not to cause extreme liquid diffusion in the transverse direction, liquid diffusion from the center absorbent element 10 to the side absorbent element 15 may be suppressed.

As will be described later, the center absorbent sheet 11 may be three-dimensionally shaped such that an original flat absorbent sheet material 24 is held between molding rolls. Since a tensile stress acts on the side walls 25b of the projections 25 during such shaping into three-dimensional configuration, fibers constituting the side walls 25b are pulled apart from each other. Therefore, the fiber density in the side walls 25b may be lower than those in the tops of the projections 25, the bottoms 31a of the longitudinal guide grooves 31, and the bottoms 32a of the transverse guide grooves 32. In some of the side walls 25b, the absorbent sheet material 24 may be ruptured to have relatively large holes.

When the side walls 25b has a low fiber density as well as the side walls 25b are formed with holes due to sheet rupture, as set forth above, the tops 25a of the projections 25 and the bottoms 31a of the longitudinal guide grooves 31 may have a thickness of 0.35 mm, a basis weight of 80 g/m$^2$ and a density of 0.22 g/cm$^3$, while the side walls 25b may have a thickness of 0.75 mm and a density of about 0.11 g/cm$^3$, for example. That is, the density of the side walls 25b may be 0.3-0.7 times that of the tops 25a and the bottoms 31a.

Accordingly, liquid migrating along the longitudinal direction through the longitudinal guide grooves 31 may easily pass through the side walls 25a into the hollows 33 of the projections 25, so that the liquid may be rapidly introduced into the underlying liquid absorption/retention layer 22, enabling rapid transfer of liquid applied to the longitudinal guide grooves 31 into the liquid absorption/retention layer 22. In addition, since the tops 25a of the projections 25, the bottoms 31a of the longitudinal guide grooves 31 and the bottoms 32a of the transverse guide grooves 32 may be kept at a relatively high fiber density, the wet tensile breaking strength of the whole center absorbent sheet 11 may be increased so that even when a body pressure is applied thereto, the three-dimensional configuration of the center absorbent sheet 11 can be certainly maintained.

Figure 5:
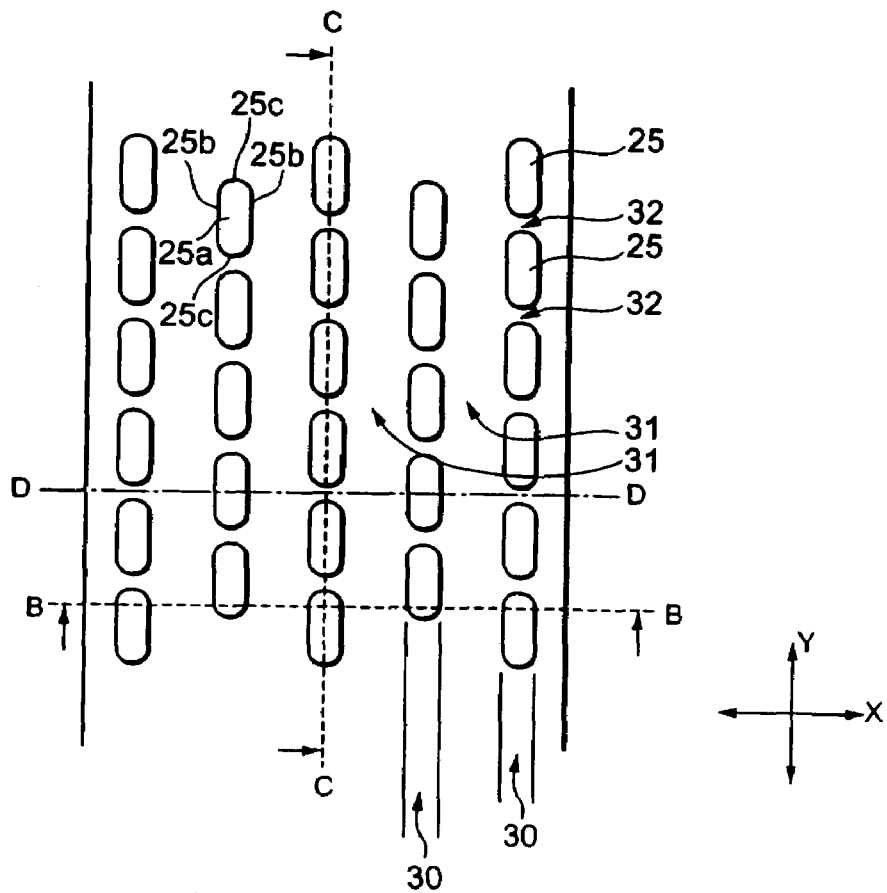
FIG. 5A is a top plan view of a portion of the center absorbent sheet shown in FIG. 4.
FIG. 5B is a sectional view taken along the line B-B, showing a portion of the center absorbent sheet of FIG. 5A on an enlarged scale.
FIG. 5C is a sectional view taken along the line C-C, showing a portion of the center absorbent sheet of FIG. 5A on an enlarged scale.
Figure 5:
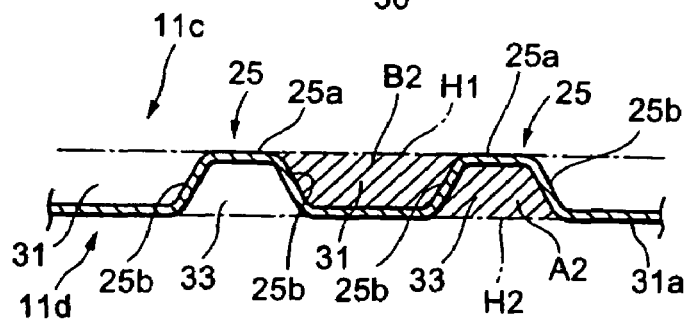
Figure 5:
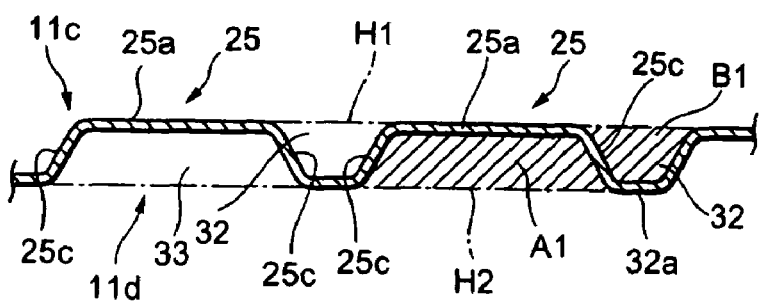

Between adjacent rows 30, as shown in FIGS. 4 and 5, the projections 25 are staggered with respect to each other in the longitudinal direction so that the transverse guide grooves 32 do not lie on a common transversely extending straight line. With the transverse guide grooves 32 thus arranged, even if a large amount of liquid is applied in a short period of time, extreme transverse liquid diffusion in the center absorbent sheet 11 can be prevented effectively.

Figure 6:
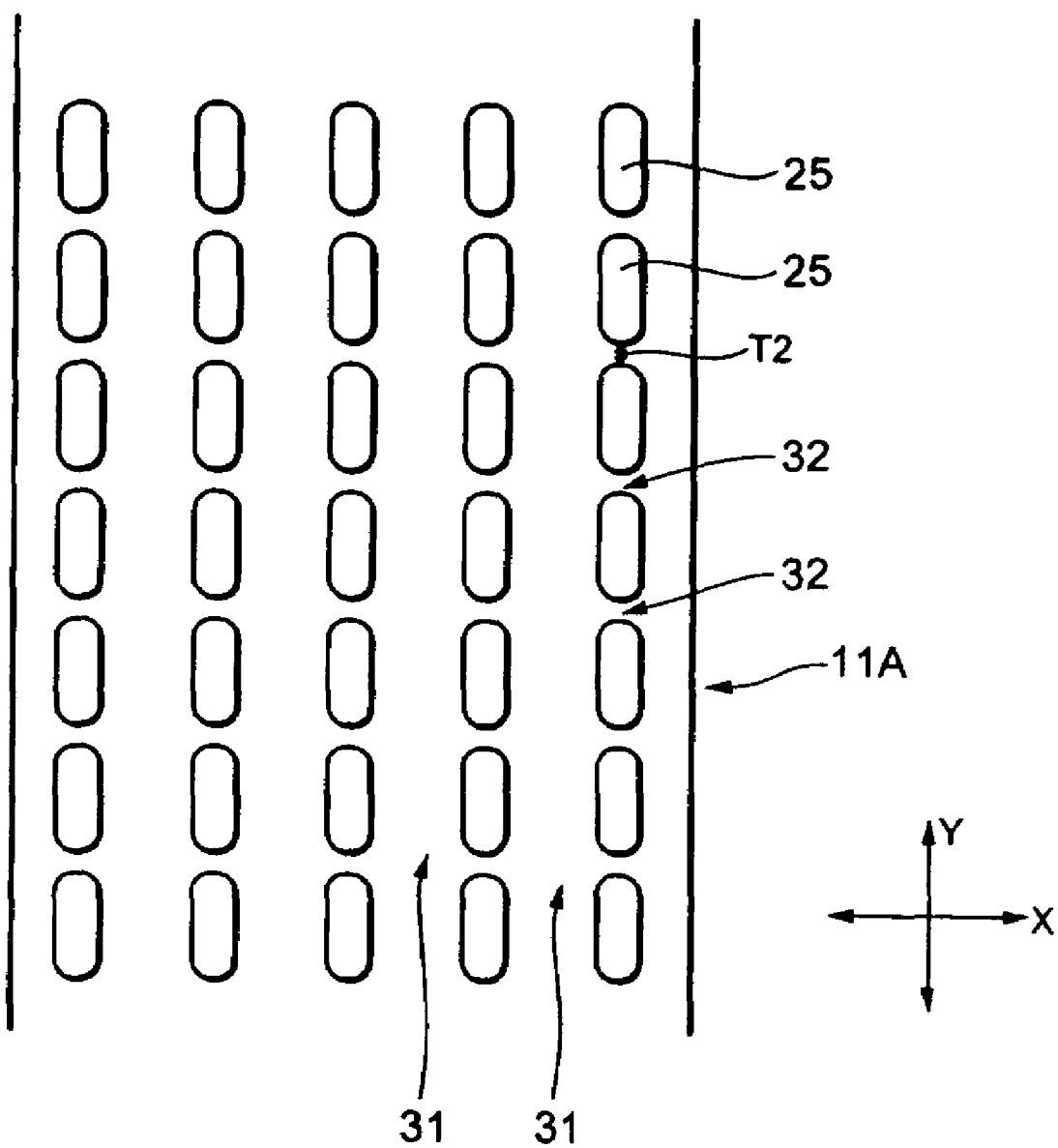
FIG. 6 is a top plan view of a portion of a center absorbent sheet according to a second embodiment.

In the present invention, however, the projections 25 should not be construed as limited to the arrangement shown in FIGS. 4 and 5, but may be arranged in various ways. For example, FIG. 6 shows a center absorbent sheet 11A according to a second embodiment, wherein between adjacent rows 30, the projections 25 are aligned also in the transverse direction so that transverse guide grooves 32 lie on a common transversely extending straight line. Preferred ranges of the individual sectional areas A1, B1, A2, B2 in this case, as well as preferred ranges of the sectional area ratios, are identical to those of the center absorbent sheet 11.

It is also possible to arrange the projections 25 with the pattern shown in FIG. 5A and the pattern shown in FIG. 6 being mixed on the center absorbent sheet. In this case, it is preferred that the pattern shown in FIG. 6 is adopted for a central portion, which is limited within a given range in the transverse direction about the longitudinally extending centerline Oy-Oy, permitting transverse liquid diffusion to some extent as well as facilitating longitudinal diffusion, while the pattern shown in FIG. 5A is adopted for side portions, which are at opposite sides of the central portion, suppressing transverse liquid migration.

In this construction, liquid may be absorbed and transferred to the liquid absorption/retention layer 22 over a large area in the central portion, while transverse liquid leakage, i.e., migration of liquid into the side absorbent elements 15 may be blocked in the side portions.

Figure 7:
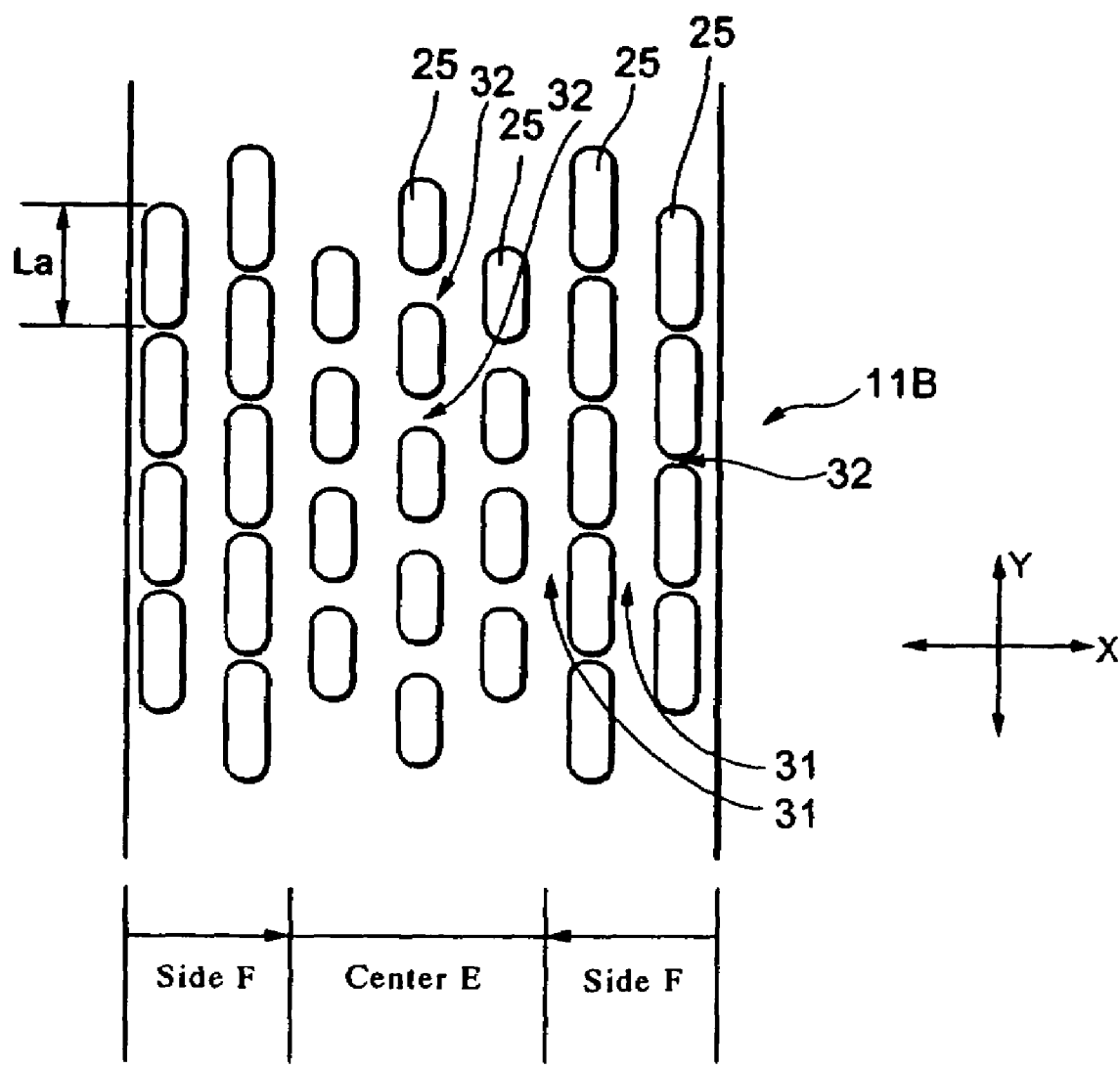
FIG. 7 is a top plan view of a portion of a center absorbent sheet according to a third embodiment.

FIG. 7 is a top plan view showing a center absorbent sheet 11B according to a third embodiment.

In the center absorbent sheet 11B of FIG. 7, the projections 25 are different in size and pattern between a central portion E, which is limited within a given range in the transverse direction about the longitudinally extending centerline Oy-Oy, and side portions F, F, which are at opposite sides of the central portion E.

Here, the width of the transverse guide groove 32 is increased in the central portion E, but decreased in the side potions F, F. That is, B1/A1 (i.e., the ratio of the sectional area B1 to the sectional area A1 in FIG. 5C) is smaller in the side portions F than in the central portion E. In the central portion E, accordingly, liquid is allowed to easily pass through the transverse guide grooves 32 and diffuse in the transverse direction toward a next longitudinal guide groove 31. In the side portions F, on the other hand, liquid is allowed to diffuse mainly along the longitudinal direction through the longitudinal guide grooves 31 because it is not easy to pass through the transverse guide grooves 32.

Moreover, the longitudinal dimension La of the projection 25 is decreased in the central portion E, but increased in the side potions F, so that liquid trying to flow in the transverse direction may be easily blocked by the projections 25 in the side portions F.

The width of the longitudinal guide groove 31 may optionally be increased in the central portion E, but decreased in the side potions F so as to increase the density of the projections 25 in the transverse direction more in the side portions F than in the central portion E. That is, B2/A2 (i.e., the ratio of the sectional area B2 to the sectional area A2 in FIG. 5B) may be smaller in the side portions F than in the central portion E.

In the central portion E, liquid may be diffused over a relatively large area while being guided mainly in longitudinal movement, so that liquid can be rapidly absorbed by the center absorbent sheet 11 and transferred into the liquid absorption/retention layer 22. In the side portions F, on the other hand, transverse migration of liquid may be effectively prevented.

Figure 8:
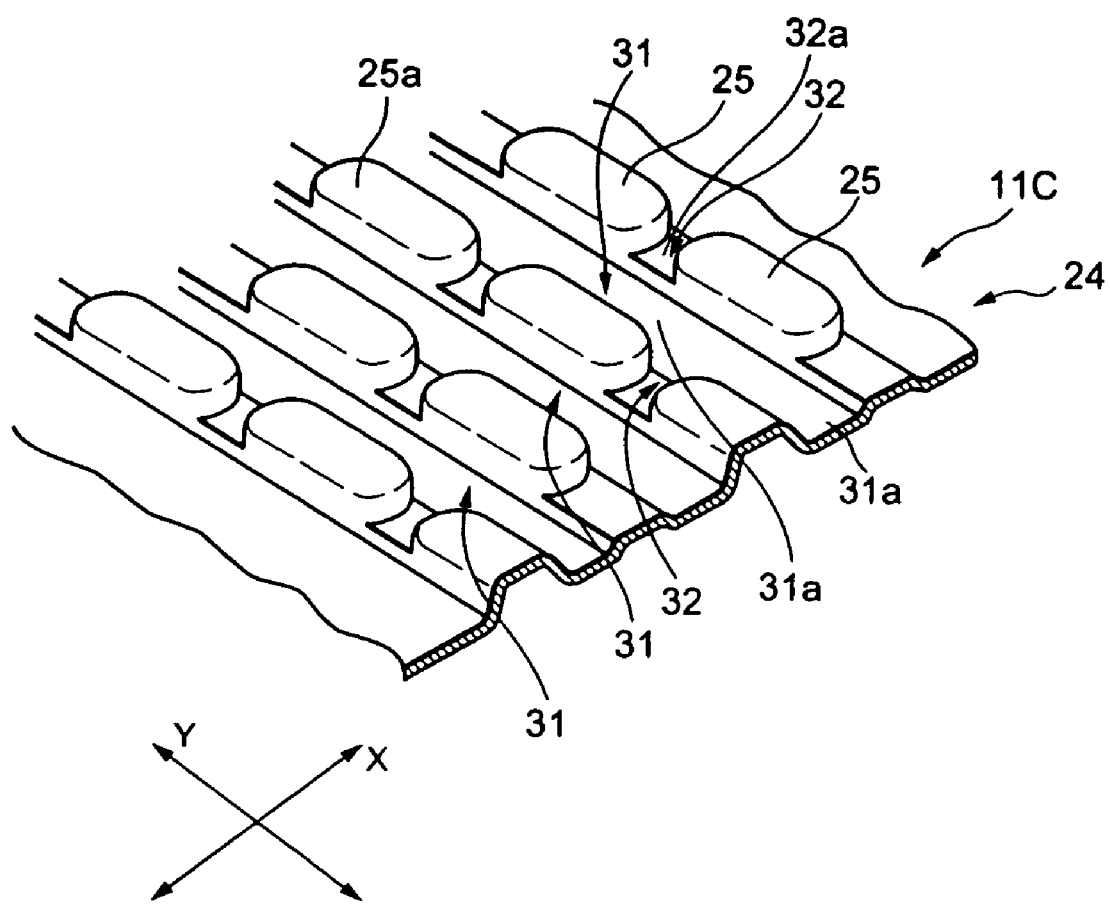
FIG. 8 is a top plan view of a portion of a center absorbent sheet according to a fourth embodiment.

FIG. 8 is a perspective view showing a center absorbent sheet 11C according to a fourth embodiment of the present invention.

In the center absorbent sheet 11C, the bottoms 32a of the transverse guide grooves 32 are positioned slightly higher than the bottoms 31a of the longitudinal guide grooves 31. That is, the transverse guide grooves 32 are shallower than the longitudinal guide grooves 31 when the depth of the groove is measured from the tops 25a of the projections 25. With the center absorbent sheet 11C, liquid can easily be diffused along the longitudinal direction through the longitudinal guide grooves 31, wherein only when a large amount of liquid is applied to the longitudinal guide grooves 31, liquid may be guided in transverse movement through the transverse guide grooves 32.

The side absorbent sheet 16 provided in the side absorbent element 15 is not formed with the projections 25 and has a flat skin-side surface, unlike the center absorbent sheet 11. The side absorbent sheet 16 may be formed of material similar to or different from that of the center absorbent sheet 11.

The second topsheet 13 and the third topsheet 18 are of a relatively bulky sheet formed with voids for passage of liquid, such as through-air bonded nonwoven fabric comprising sheath/core bicomponent synthetic fibers, of which the core is polypropylene (PP) and the sheath is polyethylene (PE). The through-air bonded nonwoven fabric may have a basis weight of about 15 to 50 g/m².

The second and the third topsheets 13, 18 may have a lower fiber density than the center and the side topsheets 12, 17, and the fiber density of the second and the third topsheets 13, 18 may be 0.016 to 0.08 g/cm³.

The soft sheet 23 is also permeable to liquid and may be a through-air bonded nonwoven fabric similar to that used for the second and the third topsheets 13, 18.

The liquid absorption/retention layer 22 may be of an air-laid nonwoven fabric (air-laid pulp). The air-laid nonwoven fabric may be manufactured such that after pulp fibers are laid to have a basis weight within the range of 50 to 300 g/m², a heat fusible binder such as acrylic resin is dispersed therein in an amount of 5 to 20% by weight of the whole nonwoven fabric and then heated for bonding the pulp fibers to each other. Here, the air-laid nonwoven fabric may contain synthetic fibers, such as polyester (PET) having a fineness of 1.6 to 4.4 dtex and a fiber length of 1 to 10 mm, in an amount of 5 to 50% by weight, providing high wet strength to maintain bulkiness even after liquid absorption.

Preferably, the air-laid nonwoven fabric may further contain superabsorbent polymer (SAP) in an amount of 5 to 50 g/m², so as to improve the liquid absorption/retention layer 22 in the ability to absorb and retain liquid.

Preferably, the liquid absorption/retention layer 22 may have a higher density than the center absorbent sheet 11, wherein the density of the liquid absorption/retention layer 22 preferably falls within the range of 0.08 to 0.15 g/cm³.

Alternatively, the liquid absorption/retention layer 22 may be a polymer sheet, wherein superabsorbent polymer of about 10 to 70 g/m² is wrapped in tissue of about 15 to 30 g/m². It is also possible to wrap pulp fibers in tissue, followed by compression to have a density within the range of 0.08 to 0.15 g/cm³, wherein superabsorbent polymer of about 10 to 70 g/m² is dispersed in the pulp fibers of 50 to 300 g/m².

Figure 9:
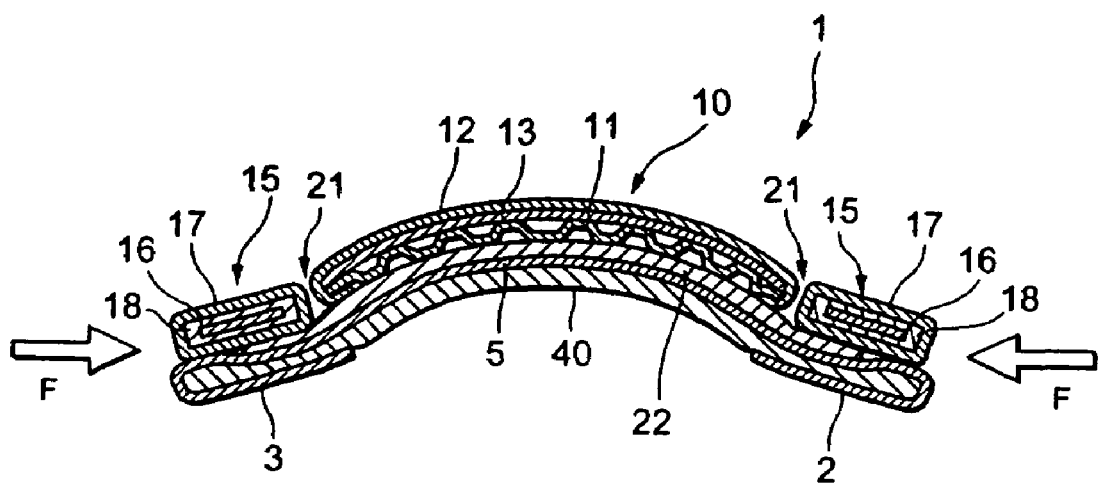
FIG. 9 is a sectional view taken along the transverse reference line, showing a state where the sanitary napkin of FIG. 1 is attached to a groin piece of an undergarment.

FIG. 9 is a sectional view showing a state where the sanitary napkin 1 of the first embodiment is attached to an inner side of a crotch portion 40 of a short panty.

When the sanitary napkin 1 is to be worn, it is fixed to the inner side of the crotch portion 40 through the pressure-sensitive adhesive layers 6 disposed on the garment-side surface of the backsheet 5. Subsequently, the wings 2, 3 are folded back at side edges of the crotch portion 40 and laid on an outer side of the crotch portion 40. These wings 2, 3 are fixed to the outer side of the crotch portion 40 through the pressure-sensitive adhesive layers 7, 7 disposed on the garment-side surface.

When the sanitary napkin 1 is attached to the crotch by wearing the short panty, a clamping force F, F will be exerted by the thighs on the crotch portion 40 and the sanitary napkin 1 from both sides thereof. Due to the clamping force F, F, the sanitary napkin 1 may be deformed to bring the side edges 1c, 1d closer together. At this time, since the sanitary napkin 1 can be easily folded at the boundaries 21, 21, the center absorbent element 10 tends to be deformed to project toward the wearer's body, coming into close contact with the genital organs. On the other hand, since the side absorbent elements 15, 15 are of a small width, they are able to come into close contact with the labia majora or the outside thereof without being unduly deformed.

Menstrual blood discharged from the genital organs is to be applied to the skin-side surface of the center absorbent element 10. The menstrual blood may pass through the center topsheet 12, pass through the second topsheet 13 via voids under gravitation, and reach the center absorbent sheet 11 for absorption. Subsequently, the menstrual blood permeating through the center absorbent sheet 11 may be introduced into and retained by the underlying liquid absorption/retention layer 22. When a large amount of menstrual blood is applied to the center topsheet 12 in a short period of time, it may be temporarily stored in the longitudinal guide grooves 31 of the center absorbent sheet 11, preventing liquid from staying for a long time in the center topsheet 12 and the second topsheet 13.

Menstrual blood introduced into the longitudinal guide grooves 31 of the center absorbent sheet 11 may permeate through the bottoms 31a of the longitudinal guide grooves 31 into the liquid absorption/retention layer 22, as well as pass through low-density portions of the side walls 25b of the longitudinal guide grooves 31 into the hollows 33 of the projections 25 for subsequent rapid absorption by the liquid absorption/retention layer 22. If a large amount of menstrual blood is introduced into one longitudinal guide groove 31, the menstrual blood may migrate along the longitudinal direction (Y-direction) through the longitudinal guide groove 31, as well as migrate to a next longitudinal guide groove 31 through transverse guide grooves 32 so as to diffuse along the longitudinal direction also through this longitudinal guide groove 31 for subsequent absorption by the liquid absorption/retention layer 22. That is, although liquid tends to diffuse mainly in the longitudinal direction, but is also allowed to migrate in the transverse direction to some extent, thereby preventing liquid from concentrating and staying in only a few of the longitudinal guide grooves 31.

In the sanitary napkin 1, furthermore, since the center absorbent element 10 is provided independently centrally of the sanitary napkin 1, the boundaries 21, 21 may function to prevent menstrual blood from flowing out. Migration of liquid from the center absorbent element 10 into the side absorbent element 15 may also be blocked by the compressed/recessed portions 14.

It should be noted that the center topsheet 12 and the side topsheet 17 may be in contact with each other along the boundaries 21, 21, wherein because the side topsheet 17 has a lower liquid permeation rate than the center topsheet 12, menstrual blood absorbed by the center absorbent element 10 will be hardly transferred to the side absorbent elements 15, 15 even if it reaches the boundaries 21, 21 through the center topsheet 12.

In the sanitary napkin 1 which is intended to receive menstrual blood on the center absorbent element 10, accordingly, the skin-side surface of the side absorbent elements 15 may be kept dry as long as menstrual blood is properly applied to the sanitary napkin 1. Here, the liquid absorption/retention layer 22 extends over a large area so as to be positioned not only beneath the center absorbent element 10 but beneath the side absorbent elements 15, as shown in FIG. 2. Therefore, menstrual blood introduced into the liquid absorption/retention layer 22 through the center absorbent element 10 may migrate to a position beneath the side absorbent elements 15.

If menstrual blood flowing down the wearer's crotch comes into direct contact with the side topsheet 17 of the side absorbent element 15, of course, it may be passed through the side topsheet 17 and the third topsheet 18 and then absorbed by the side absorbent sheet 16.

Hereinbelow, preferred ranges of dimensions will be described. The following dimensions are values measured with the sanitary napkin 1 being developed in a free state where no external force is exerted.

The sanitary napkin 1 has an overall length of 180 to 350 mm along the longitudinally extending centerline Oy-Oy and a width of 60 to 110 mm at a position where the right side edge 1c and the left side edge 1d are nearest in the transverse direction.

The center absorbent element 10 has a width W1 (see FIG. 2), which preferably falls within the range of 20 to 70 mm. If it is less than 20 mm, the center absorbent element 10 may possibly be displaced from the vaginal opening in the transverse direction during wear, making it difficult to ensure close contact between the skin-side surface of the center absorbent element 10 and the vaginal opening. In addition, both side portions of the center absorbent sheet 11 may possibly be saturated at an early stage with menstrual blood diffusing in the transverse direction within the center absorbent sheet 11. If it is greater than 70 mm, on the other hand, the side absorbent elements 15, 15 may have an extremely small width W2 (see FIG. 2), causing transverse leakage of menstrual blood beyond the side absorbent elements 15, 15.

The width W2 of the side absorbent elements 15, 15 preferably falls within the range of 5 to 30 mm. If it is less than 5 mm, menstrual blood absorbed by the center absorbent sheet 11 may easily leak out of the sanitary napkin 1 transversely beyond the side absorbent elements 15, 15. If it is greater than 30 mm, on the other hand, the width of the sanitary napkin 1 may be too large, or the width W1 of the center absorbent element 10 maybe too small, reducing the liquid absorption capacity of the center absorbent element 10 too much.

In the grooves along the boundaries 21, 21, the clearance between the center topsheet 12 and the side topsheet 17 is preferably at most 5 mm. They may be in contact with each other without overlapping, as shown in FIG. 3. If the center absorbent element 10 and the side absorbent elements 15 overlap each other, the side topsheets 17 subjected to the transverse clamping force F, F shown in FIG. 9 may be strongly pressed against the center topsheet 12 at the boundaries 21, 21, so that menstrual blood absorbed by the center absorbent sheet 11 may easily be passed through the center topsheet 12 and the side topsheet 17 and diffused into the side absorbent sheet 16, at the boundaries 21, 21.

Next, a process for shaping the center absorbent sheet 11 into the three-dimensional configuration shown in FIG. 4 will be described.

Figure 10:
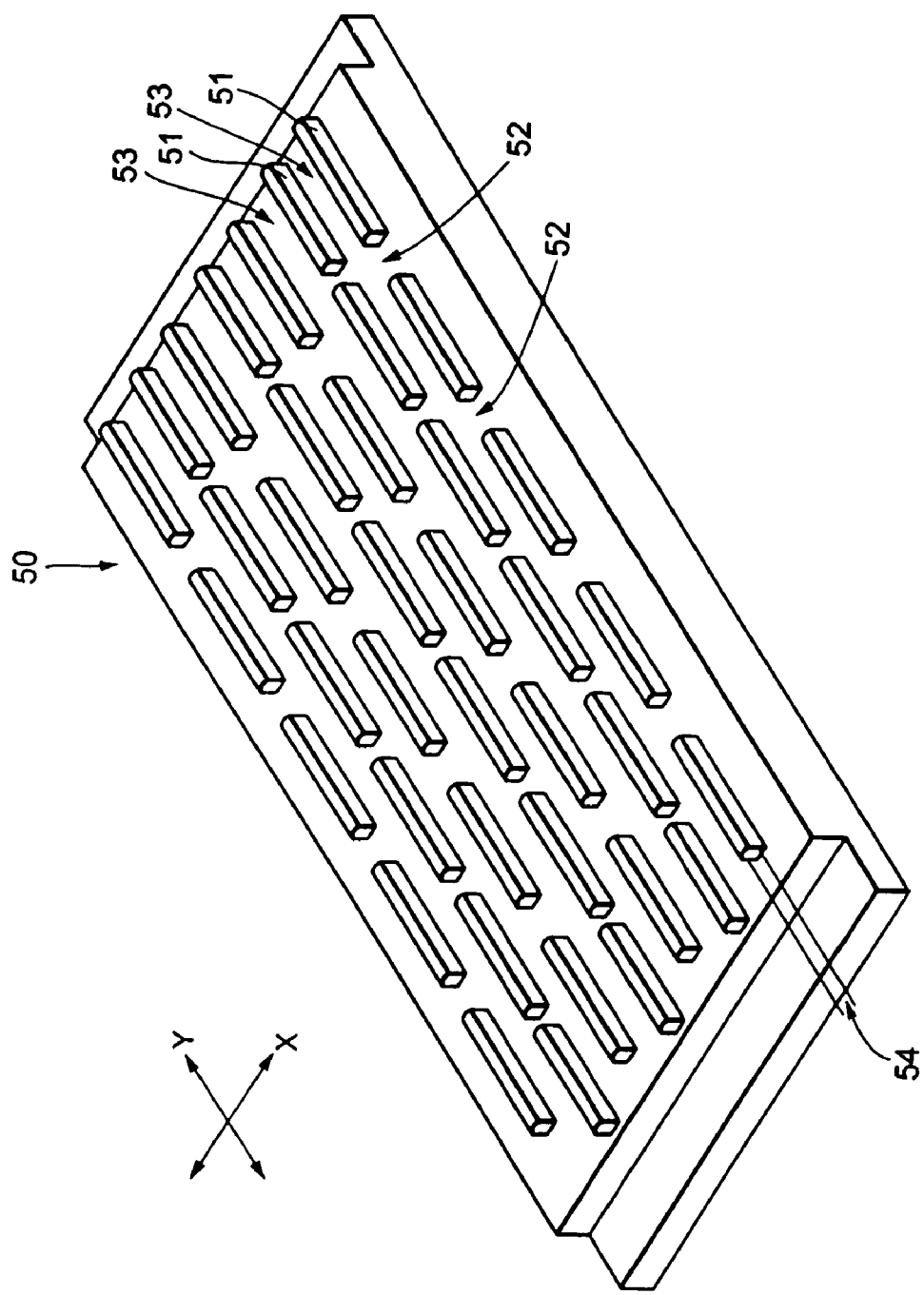
FIG. 10 is a perspective view of a lower mold for three-dimensional shaping of the center absorbent sheet.
Figure 11:
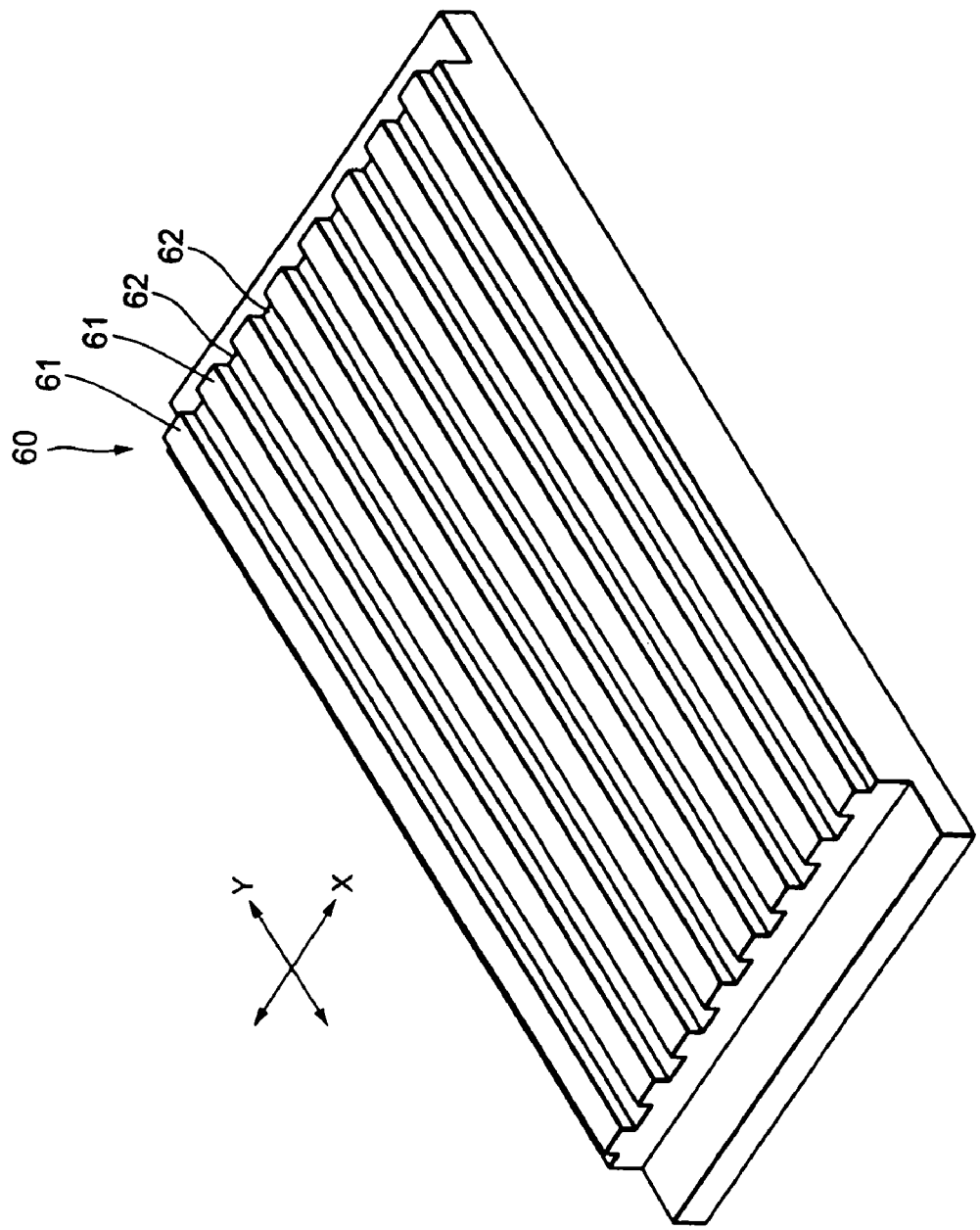
FIG. 11 is a perspective view of an upper mold for three-dimensional shaping of the center absorbent sheet.

FIG. 10 is a perspective view showing a lower mold 50 and FIG. 11 is a perspective view showing an upper mold 60.

In the lower mold 50 shown in FIG. 10, a plurality of projections 51 are aligned in the longitudinal direction (Y-direction) with transverse grooves 52 therebetween, thereby forming rows 54. These rows 54 alternating with longitudinal grooves 53 in the transverse direction (X-direction) are parallel to each other. Between adjacent rows 54, the transverse grooves 52 do not lie on a common transversely extending straight line.

The upper mold 60 shown in FIG. 11 is formed with parallel projections 61, each extending continuously in the longitudinal direction (Y-direction). Between adjacent projections 61, grooves 62 are defined. The pitch of the rows 54 arranged in the transverse direction of the lower mold 50 is equal to the pitch of the grooves 62 arranged in the transverse direction of the upper mold 60.

Figure 12:
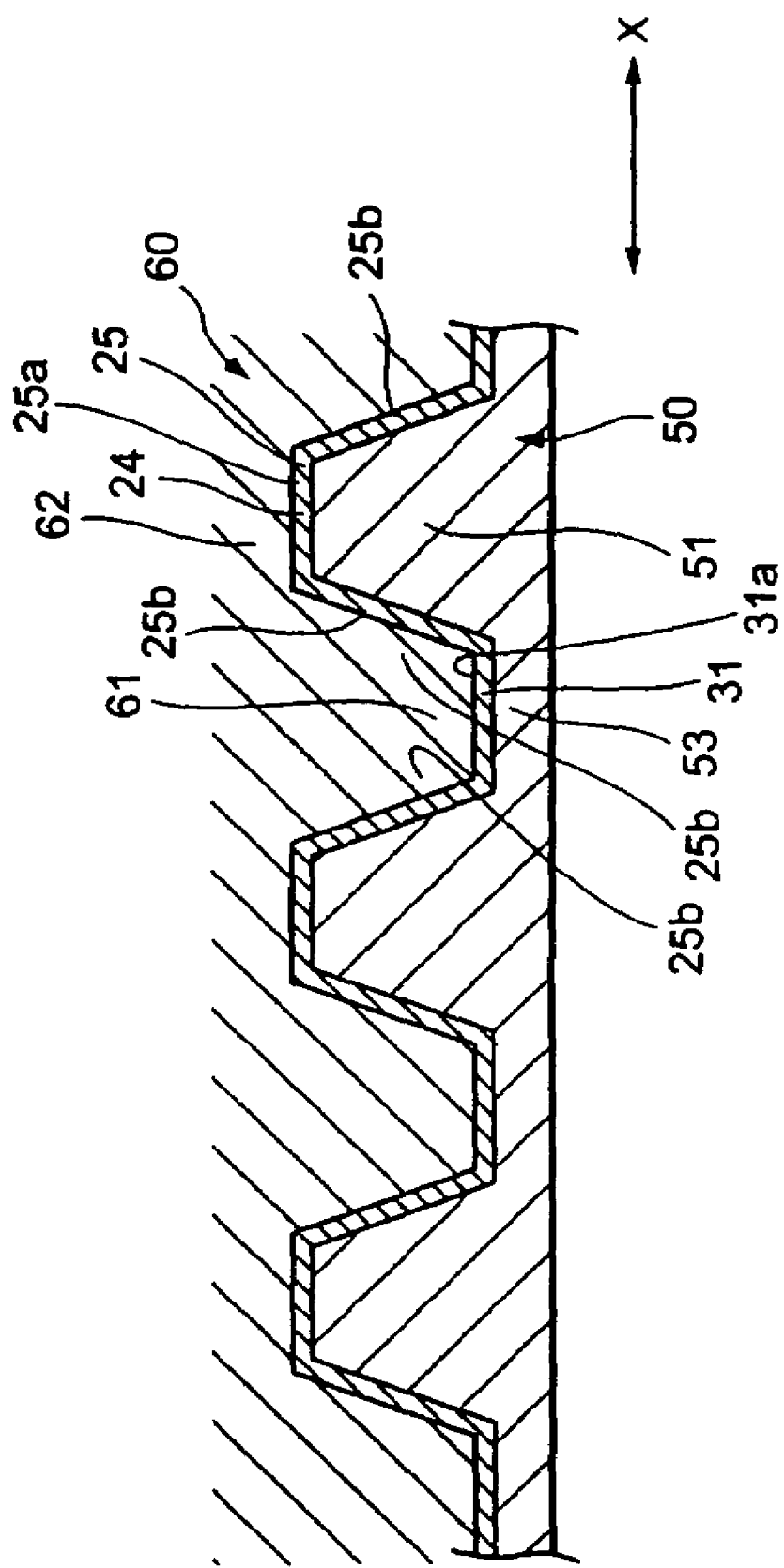
FIG. 12 is a sectional view showing a state where the center absorbent sheet is being three-dimensionally shaped between the upper and the lower molds.

With the surfaces of the lower and the upper molds 50, 60 being heated to a temperature of about 120 degrees centigrade, the absorbent sheet material 24 is held between the lower and the upper molds 50, 60, as shown in the sectional view of FIG. 12. The lower and the upper molds 50, 60 mesh such that the projections 51 engage in the grooves 62 and the projections 61 engage in the longitudinal grooves 53. It should be noted that the lower and the upper molds 50, 60 are so assembled as to leave a slight clearance both between the tops of the projections 51 of the lower mold 50 and the bottoms of the grooves 62 of the upper mold 60 and between the tops of the projections 61 of the upper mold 60 and the bottoms of the longitudinal grooves 53 of the lower mold 50.

As a result, the projections 25 and the longitudinal guide grooves 31 are formed in the absorbent sheet material 24 (by means of the projections 51 of the lower mold 50 and the projections 61 of the upper mold 60, respectively), as shown in FIG. 12. In addition, since the absorbent sheet material 24 will not receive a large tensile force at locations facing the transverse grooves 52 of the lower mold 50 when the lower and the upper molds 50, 60 are pressed against each other, the absorbent sheet material 24 tends to be kept relatively flat at locations facing the transverse grooves 52. This results in formation of the transverse guide grooves 32 between longitudinally adjacent projections 25. Accordingly, the transverse guide grooves 32 tend to be shallower than the longitudinal guide grooves 31 when the depth of the groove is measured from the tops 25a of the projections 25, as shown in FIG. 8.

At this time, tensile stresses in both X- and Y-directions concentrate in the portions that will be the side walls 25b of the projections 25. Therefore, fibers for constituting the side walls 25b are pulled apart from each other, providing the side walls 25b with the low-fiber density portions.

When the center absorbent sheet 11 is to be mass-produced, the upper mold 60 shown in FIG. 11 may be modified for a roll surface with the Y-direction along a circumferential direction and the X-direction along an axial direction and the lower mold 50 shown in FIG. 10 be likewise modified for a roll surface with the Y-direction along a circumferential direction and the X-direction along an axial direction, wherein two rolls are opposed to each other with a clearance therebetween so that the absorbent sheet material 24 may be supplied in between them to form the center absorbent sheet 11.

Hereinabove, the center absorbent sheet 11 has been described as being of a single absorbent sheet material, but may also be formed of a stack of two or more absorbent sheet materials. In the side walls 25b of the center absorbent sheet 11, as has been described above, constituent fibers are pulled apart from each other due to a tensile force exerted during shaping into a three-dimensional configuration, which may possibly result in formation of ruptures in the side walls 25b. At this time, if a stack of two or more absorbent sheet materials 24 is used, these absorbent sheet materials 24 may have low-fiber density portions or ruptures at different locations in the individual side walls 25b. Therefore, the side walls 25b themselves may be prevented from lowering in strength, easily keeping the three-dimensional configuration even when wet.

The absorbent article according to the present invention may also be constructed such that a topsheet of an apertured resin film is adhered to a skin-side surface of an absorbent sheet that is three-dimensionally shaped similarly to the center absorbent sheet 11. The absorbent article may be made thin without providing the liquid absorption/retention layer 22, wherein liquid will be absorbed only by the absorbent sheet.

Figure 13:
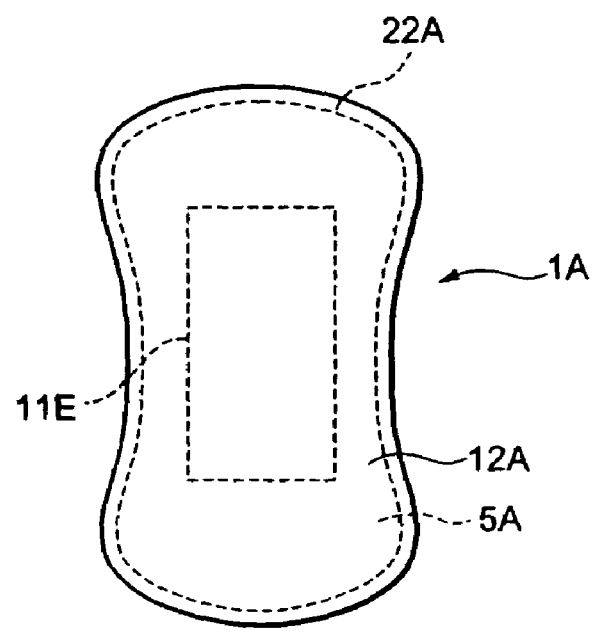
FIGS. 13A and 13B are top plan views showing still further embodiments of the absorbent article according to the present invention.
Figure 13:
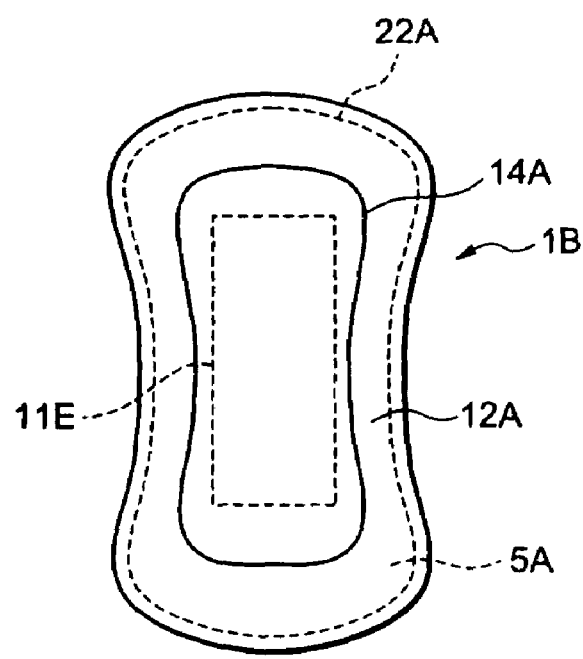

The absorbent article according to the present invention may also be embodied in a sanitary napkin 1A shown in FIG. 13A and a sanitary napkin 1B shown in FIG. 13B.

In the sanitary napkin 1A shown in FIG. 13A, a liquid-permeable topsheet 12A and a backsheet 5A are both of an hourglass shape, and a liquid absorption/retention layer 22A, which is of a similar hourglass shape, is interposed between the topsheet 12A and the backsheet 5A. Between the topsheet 12A and the liquid absorption/retention layer 22A, furthermore, there is disposed an absorbent sheet 11E that is smaller than the liquid absorption/retention layer 22A. This absorbent sheet 11E is similar to the center absorbent sheets 11, 11A, 11B and 11C.

Since the absorbent sheet 11E is disposed in the central portion of the sanitary napkin 1A, liquid applied to the central portion may be absorbed by the absorbent sheet 11E while being guided in longitudinal movement also by the absorbent sheet 11E, and subsequently, absorbed by the underlying liquid absorption/retention layer 22A. Thus, transverse leakage may be effectively prevented.

The sanitary napkin 1B shown in FIG. 13B is identical to the sanitary napkin 1A shown in FIG. 13A except that a compressed/recessed portion 14A is formed therein. In the compressed/recessed portion 14A, the topsheet 12A, as well as the liquid absorption/retention layer 22A, is compressed and recessed. Although the compressed/recessed portion 14A is formed to surround the absorbent sheet 11E in the embodiment shown in FIG. 13B, it should not be limited thereto. For example, left and right portions of the compressed/recessed portion 14A may be separate and distinct from each other.

In this embodiment, the compressed/recessed portion 14A, whose left and right portions are located outside transversely opposite sides of the absorbent sheet 11E, may also guide liquid in longitudinal movement, preventing transverse liquid leakage more effectively.

EXAMPLES

As Examples and Comparative Examples, various absorbent sheets were prepared as follows. Air-laid pulp having a basis weight of 80 g/m² was used as a common absorbent sheet material, wherein the air-laid pulp was manufactured by air-laying pulp fibers and adding acrylic resin as binder in an amount of 8% by weight. In Comparative Example 2 and Examples 1-4, ribs and projections due to three-dimensional shaping had a thickness of 0.35 mm and a density of 0.22 g/cm³ at tops of the ribs or projections and a thickness of 0.75 mm and a density of 0.11 g/cm³ at side walls of the ribs or projections.

Comparative Example 1

The absorbent sheet material was used as absorbent sheet without three-dimensional shaping.

Comparative Example 2

The absorbent sheet material was three-dimensionally shaped as shown in FIG. 14. The absorbent sheet shown in FIG. 14 was constructed such that longitudinal ribs 70 continuing in the longitudinal direction without interruption and longitudinal guide grooves 71 adjacent thereto alternate with each other in the transverse direction. The longitudinal guide grooves 71 had a width of 2 mm in the transverse direction (X-direction), the longitudinal ribs 70 had a width of 1.5 mm in the transverse direction (X-direction), and the longitudinal ribs 70 had a height of 2 mm.

Comparative Example 3

The absorbent sheet material was three-dimensionally shaped as shown in FIG. 15A. As shown in FIG. 15B, the absorbent sheet was formed with a plurality of projections 80 in the form of a truncated cone. The projections 80 had a diameter of 2 mm at upper surfaces and a height of 2 mm and a diameter of 3.5 mm at bases. The base-to-base distance between adjacent projections 80 was 0.6 mm, as shown in FIG. 15C.

Example 1

The absorbent sheet material was three-dimensionally shaped as shown in FIG. 6. The projections 25 had a width of 3.5 mm in the transverse direction (X-direction) and a length of 7 mm in the longitudinal direction (Y-direction), at the tops 25a, and a height of 2 mm. The transverse guide grooves 32 had a width of 3 mm at the bottoms 32a, and the longitudinal guide grooves 31 had a width of 3 mm at the bottoms 31a.

Example 2

The absorbent sheet material was three-dimensionally shaped as shown in FIGS. 4 and 5. The projections 25 had a width of 3.5 mm in the transverse direction (X-direction) and a length of 7 mm in the longitudinal direction (Y-direction), at the tops 25a, and a height of 2 mm. The transverse guide grooves 32 had a width of 3 mm at the bottoms 32a, and the longitudinal guide grooves 31 had a width of 3 mm at the bottoms 31a.

Example 3

The absorbent sheet material was three-dimensionally shaped as shown in FIGS. 4 and 5. The projections 25 had a width of 2 mm in the transverse direction (X-direction) and a length of 5 mm in the longitudinal direction (Y-direction), at the tops 25a, and a height of 2 mm. The transverse guide grooves 32 had a width of 3 mm at the bottoms 32a, and the longitudinal guide grooves 31 had a width of 3 mm at the bottoms 31a.

Example 4

The absorbent sheet material was three-dimensionally shaped as shown in FIGS. 4 and 5. The projections 25 had a width of 2 mm in the transverse direction (X-direction) and a length of 10 mm in the longitudinal direction (Y-direction), at the tops 25a, and a height of 2 mm. The transverse guide grooves 32 had a width of 3 mm at the bottoms 32a, and the longitudinal guide grooves 31 had a width of 3 mm at the bottoms 31a.

(Absorbency Testing Method 1)

The individual absorbent sheets were cut to have a width of 100 mm in the transverse direction (X-direction) and a length of 200 mm in the longitudinal direction (Y-direction). Then, air-laid pulp containing superabsorbent polymer (SAP) in an amount of 20% by weight and having a basis weight of 200 g/m² was cut into the same size as the absorbent sheet and laid beneath the absorbent sheet.

Then, 7 g of artificial menstrual blood was dropped on the surface of the absorbent sheet at a rate of 7 g/min with an auto burette.

After completion of dropping, the sample was allowed to stand for one minute, and then, the artificial menstrual blood diffused on the surface of the absorbent sheet was measured for diffusion dimensions in the transverse direction (CD) and the longitudinal direction (MD). The test results are shown in Table 1.

TABLE 1

| | Com. Ex. 1 | Com. Ex. 2 | Com. Ex. 3 | Ex. 1 | Ex. 2 | Ex. 3 | Ex. 4 |
|---|---|---|---|---|---|---|---|
| MD | 50 | 93 | 62 | 70 | 70 | 73 | 75 |
| CD | 50 | 40 | 58 | 50 | 48 | 40 | 40 | unit: mm

In Comparative Example 1, as shown in Table 1, the diffusion dimension of the artificial menstrual blood in the transverse direction (CD) and the diffusion dimension of the artificial menstrual blood in the longitudinal direction (MD) are equal; also in Comparative Example 3, the diffusion dimension of the artificial menstrual blood in the transverse direction (CD) and the diffusion dimension of the artificial menstrual blood in the longitudinal direction (MD) are nearly equal. In Comparative Example 2, the diffusion dimension of the artificial menstrual blood in the longitudinal direction (MD) is about twice the diffusion dimension of the artificial menstrual blood in the transverse direction (CD).

In all Examples 1-4, on the other hand, the diffusion dimension of the artificial menstrual blood in the longitudinal direction (MD) is larger than the diffusion dimension of the artificial menstrual blood in the transverse direction (CD), wherein Examples 1-4 are not as large in the diffusion dimension in the longitudinal direction (MD) as Comparative Example 2, but are smaller in the diffusion dimension in the transverse direction (CD) than Comparative Examples 1 and 3. In Examples 1-4, the diffusion dimension in the transverse direction (CD) is small, as well as the artificial menstrual blood diffusing along the longitudinal direction is rapidly introduced into the air-laid nonwoven fabric beneath the absorbent sheet, as compared with Comparative Example 2.

Next, the absorbent sheets for Comparative Examples 1-3 and Examples 1-4 were individually incorporated into a sanitary napkin, and then, absorbency was measured.

(Structure of Sanitary Napkin)

Air-laid pulp containing superabsorbent polymer in an amount of 20% by weight and having a basis weight of 200 g/m² was cut to have a width of 80 mm in the transverse direction and a length of 200 mm in the longitudinal direction and laid on a liquid-impermeable backsheet. The individual absorbent sheets for Comparative Examples 1-3 and Examples 1-4 were cut to have a width of 80 mm in the transverse direction and a length of 150 mm in the longitudinal direction and laid on the air-laid pulp. Moreover, through-air bonded nonwoven sheet having a basis weight of 25 g/m² was cut to have a width of 80 mm in the transverse direction and a length of 200 mm in the longitudinal direction and laid on the absorbent sheet. Still moreover, resin film (basis weight of 25 g/m²) with hydrophilic lubricant kneaded therein in an amount of 25% by weight and a plurality of liquid passage holes formed therein was cut to have a width of 80 mm in the transverse direction and a length of 200 mm in the longitudinal direction and laid on the through-air bonded nonwoven sheet.

(Absorbency Testing Method 2)

An acrylic plate with an opening at its center was placed on the sanitary napkin. The acrylic plate was a flat plate having a thickness of 5 mm, a width of 100 mm in the transverse direction, and a length of 200 mm in the longitudinal direction, and the opening formed centrally of the acrylic plate had an opening width of 10 mm in the transverse direction and an opening length of 40 mm in the longitudinal direction.

After the acrylic plate was placed on the sanitary napkin, 3 cc of artificial menstrual blood was firstly dropped (at a drop rate of 90 ml/min) through the opening formed in the acrylic plate by means of an auto burette, and 4 cc of artificial menstrual blood was subsequently dropped (at a drop rate of 95 ml/min). After dropping 7 cc of artificial menstrual blood in total, the sample was allowed to stand for one minute, and then, the artificial menstrual blood diffused on the topsheet of the sanitary napkin was measured for diffusion dimensions in the transverse direction (CD) and the longitudinal direction (MD).

In addition to the above-mentioned test, also after the acrylic plate was placed on the sanitary napkin, 3 cc of artificial menstrual blood was firstly dropped (at a drop rate of 90 ml/min) through the opening formed in the acrylic plate by means of an auto burette, 4 cc of artificial menstrual blood was secondly dropped (at a drop rate of 95 ml/min), 3 cc of artificial menstrual blood was thirdly dropped (at a drop rate of 90 ml/min), and 4 cc of artificial menstrual blood was finally dropped (at a drop rate of 95 ml/min). After dropping 14 cc of artificial menstrual blood in total, the sample was allowed to stand for one minute, and then, the artificial menstrual blood diffused on the topsheet of the sanitary napkin was measured for diffusion dimensions in the transverse direction (CD) and the longitudinal direction (MD). The test results are shown in Table 2.

TABLE 2

|  |  | Com. Ex. 1 | Com. Ex. 2 | Com. Ex. 3 | Ex. 1 | Ex. 2 | Ex. 3 | Ex. 4 |
|---|---|---|---|---|---|---|---|---|
| 7 cc Diffusion | MD | 62 | 68 | 55 | 71 | 70 | 65 | 70 |
|  | CD | 50 | 35 | 55 | 40 | 40 | 45 | 40 |
| 14 cc Diffusion | MD | 95 | 100 | 90 | 90 | 95 | 90 | 95 |
|  | CD | 72 | 60 | 75 | 60 | 65 | 60 | 65 | unit: mm

From Table 2, it is seen that the diffusion dimension of the artificial menstrual blood in the transverse direction (CD) is smaller in the sanitary napkins of Examples 1-4 than in the sanitary napkins of Comparative Examples 1 and 3. When the sanitary napkins of Examples 1-4 are compared with the sanitary napkin of Comparative Example 2, the diffusion dimension in the longitudinal direction (MD) is smaller in Examples 1-4. That is, menstrual blood is rapidly introduced into the air-laid nonwoven sheet beneath the absorbent sheet in the sanitary napkins of Examples 1-4, as compared with the Comparative Example 2.

According to the present invention, as has been described hereinabove, liquid can be diffused along the longitudinal direction, effectively preventing transverse liquid leakage.

What is claimed is:

1. An absorbent article comprising:
   a backsheet;
   a liquid-absorbing retention layer disposed on a skin-side surface of the backsheet;
   a longitudinally-extending center absorbent element disposed on a skin-side surface of the liquid-absorbing retention layer, the center absorbent element including:
      a liquid-permeable center topsheet, and
      a center absorbent sheet for liquid absorption, having a skin-side surface and side edges both covered with the center topsheet, being three-dimensionally shaped in a thickness direction, and being provided with a plurality of projections, each of which is raised toward a skin-side surface of the center absorbent element to define a hollow opening on a garment-side surface of the center absorbent element and dimensioned to be longer in a longitudinal direction of the absorbent article than in a transverse direction of the absorbent article;
   longitudinally-extending side absorbent elements disposed on the skin-side surface of the liquid-absorbing retention layer and adjacent transversely opposite sides of the center absorbent element without overlapping the center absorbent element, each side absorbent element including:
      a liquid-permeable side topsheet, and
      a side absorbent sheet for liquid absorption, having a skin-side surface and side edges both covered with the side topsheet, wherein
   the center topsheet has either a higher liquid permeation rate or a higher hydrophilicity than the side topsheet,
   a plurality of compressed portions is formed on the center absorbent element adjacent to the side absorbent sheet, the compressed portions extending linearly in the longitudinal direction and at a constant pitch, and
   one of the side edges of the side absorbent sheet covered with the side topsheet is either opposingly spaced apart or in contact with one of the side edges covered with the center topsheet at transversely opposite sides of the center absorbent sheet, and the one side edge covered by the side topsheet and the one side edge covered by the center topsheet together define a groove formed in the skin-side surface of the absorbent article.

2. An absorbent article according to claim 1, wherein the center absorbent element has a plurality of compressed and recessed portions where the center absorbent sheet and center topsheet are fusion-bonded together, and the compressed and recessed portions are arranged at regular intervals along the transversely opposite sides of the center absorbent element.

3. An absorbent article according to claim 1, wherein the center topsheet and the side topsheet each comprise a resin film or a nonwoven fabric having pluralities of liquid passage holes, wherein the ratio of total opening area to whole sheet area for the center topsheet is greater than the ratio of total opening area to whole sheet area for the side topsheet sheet, such that the liquid permeation rate of the center topsheet is greater than the liquid permeation rate of the side topsheet.

4. An absorbent article according to claim 1, wherein a hydrophilicity imparting agent is applied to the center topsheet, such that hydrophilicity of the center topsheet is greater than the hydrophilicity of the side topsheet.

5. An absorbent article according to claim 1, wherein the center topsheet comprises a nonwoven fabric formed with liquid passage holes and the side topsheet comprises a nonwoven fabric formed without liquid passage holes, such that the liquid permeation rate of the center topsheet is greater than the liquid permeation rate of the side topsheet.

6. An absorbent article according to claim 1, wherein a water-repellant material is applied to the side topsheet, such that hydrophilicity of the center topsheet is greater than the hydrophilicity of the side topsheet.

7. An absorbent article according to claim 1, wherein the center topsheet comprises a spunlaced or through-air bonded nonwoven fabric and the side topsheet comprises a meltblown nonwoven fabric, such that hydrophilicity of the center topsheet is greater than the hydrophilicity of the side topsheet.

8. An absorbent article according to claim 1, wherein:
longitudinal guide grooves are defined between transversely adjacent projections of the center absorbent sheet,
transverse guide grooves are defined between longitudinally adjacent projections of the center absorbent sheet for communication between the longitudinal guide grooves, and
the longitudinal guide grooves are dimensioned to extend over at least two projections aligned in the longitudinal direction.

9. An absorbent article according to claim 8, wherein on a transversely extending straight line passing one transverse guide groove, the projections and transverse guide grooves alternate with each other with the longitudinal guide grooves therebetween.

10. An absorbent article according to claim 8, wherein a B2/A2 ratio is larger than a B1/A1 ratio, where A1 represents a sectional area of the hollow of each projection and B1 represents a sectional area of a hollow of each transverse guide groove with the center absorbent sheet being cut along a longitudinally extending section line which passes a top of one projection, while A2 represents a sectional area of the hollow of each projection and B2 represents a sectional area of a hollow of each longitudinal guide groove with the center absorbent sheet being cut along a transversely extending section line which crosses transversely adjacent projections.

11. An absorbent article according to claim 8, wherein a B1/A1 ratio is smaller at transversely opposite side portions of the center absorbent sheet than at a position coinciding with a longitudinally extending centerline of the article, where A1 represents a sectional area of the hollow of each projection and B1 represents a sectional area of a hollow of each transverse guide groove with the center absorbent sheet being cut along a longitudinally extending section line which passes a top of one projection.

12. An absorbent article according to claim 8, wherein a B2/A2 ratio is smaller at transversely opposite side portions of the center absorbent sheet than at a position coinciding with a longitudinally extending centerline of the article, where A2 represents a sectional area of the hollow of each projection and B2 represents a sectional area of a hollow of each longitudinal guide groove with the center absorbent sheet being cut along a transversely extending section line which crosses transversely adjacent projections.

13. An absorbent article according to claim 1, wherein the projections have such different longitudinal dimensions as to be longer at transversely opposite side portions of the center absorbent sheet than at a position coinciding with a longitudinally extending centerline of the article.

14. An absorbent article according to claim 8, wherein the liquid-absorbing retention layer is disposed on a garment-side surface of the center absorbent sheet and kept in contact with individual bottoms of the longitudinal and the transverse guide grooves of the center absorbent sheet.

15. An absorbent article according to claim 8, wherein in the center absorbent sheet, walls of the projections extending alongside the longitudinal guide grooves have a lower density than tops of the projections and the bottoms of the longitudinal and the transverse guide grooves,
longitudinal guide grooves are defined between transversely adjacent projections of the center absorbent sheet,
transverse guide grooves are defined between longitudinally adjacent projections of the center absorbent sheet for communication between the longitudinal guide grooves, and
the longitudinal guide grooves are dimensioned to extend over at least two projections aligned in the longitudinal direction.

16. An absorbent article according to claim 1, which is allowed to bend more easily at boundaries between the center absorbent element and the side absorbent elements than at the center absorbent element and at the side absorbent elements.

17. An absorbent article according to claim 1, wherein when an equal amount of liquid is applied to the skin-side surface of the center absorbent element and the skin-side surface of the side absorbent element, the center absorbent element has a higher liquid absorption rate than the side absorbent element.

18. An absorbent article according to claim 1, wherein intermediate portions to the compressed portions are recessed, the intermediate portions and the compressed portions forming a compressed groove extending linearly in the longitudinal direction.

* * * * *